US010684224B2

(12) United States Patent
Dimitriadis et al.

(10) Patent No.: US 10,684,224 B2
(45) Date of Patent: *Jun. 16, 2020

(54) METHOD AND MEANS FOR MULTISPECTRAL IMAGING

(71) Applicant: Universität Heidelberg, Heidelberg (DE)

(72) Inventors: Nikolas Dimitriadis, Mannheim (DE); Nikolaos Deliolanis, Stuttgart (DE)

(73) Assignee: Universität Heidelberg, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/316,453

(22) PCT Filed: Jun. 3, 2015

(86) PCT No.: PCT/EP2015/062448
§ 371 (c)(1),
(2) Date: Dec. 5, 2016

(87) PCT Pub. No.: WO2015/185662
PCT Pub. Date: Dec. 10, 2015

(65) Prior Publication Data
US 2017/0176336 A1    Jun. 22, 2017

(30) Foreign Application Priority Data

Jun. 5, 2014 (EP) .................................. 14171378
Mar. 24, 2015 (EP) .................................. 15160630

(51) Int. Cl.
*G01N 21/64* (2006.01)
*G01N 21/91* (2006.01)
(Continued)

(52) U.S. Cl.
CPC ......... *G01N 21/6456* (2013.01); *A61B 1/043* (2013.01); *A61B 1/0638* (2013.01);
(Continued)

(58) Field of Classification Search
CPC ........... G01N 21/6428; G01N 21/6456; G01N 21/718; G01N 21/80; G01N 21/91;
(Continued)

(56) References Cited

U.S. PATENT DOCUMENTS 6,760,105 B2 * 7/2004 Oshida ............... G01N 21/6428
250/458.1
7,904,139 B2 * 3/2011 Chance ................ A61B 5/0059
600/407

(Continued)

FOREIGN PATENT DOCUMENTS

CN        1289239      3/2001
CN      101528116 A    9/2009
(Continued)

OTHER PUBLICATIONS

International Search Report issued in PCT/EP2015/062448; dated Jun. 8, 2016.
(Continued)

*Primary Examiner* — Taeho Jo
(74) *Attorney, Agent, or Firm* — Studebaker & Brackett PC

(57) ABSTRACT

Multispectral imaging of samples, in particular of biological tissues. A method for acquisition of fluorescence images and reflection images of an object including alternatingly illuminating the object with at least a first light and a second light, wherein the first light and the second light are spectrally shaped such that at least one light has several spectral regions of high light intensity separated by spectral region(s) of low light intensity, wherein the spectral regions of the first (Continued)

light and the second light with high intensity at least partially do not overlap and wherein at least one of the two lights has at least one region of low light intensity that is of longer wavelength to the neighboring region of high light intensity, and recording at least a first image of the object and a second image of the object while illuminating the object with at least one of the lights.

20 Claims, 58 Drawing Sheets

(51) Int. Cl.
 *G01J 3/44*     (2006.01)
 *A61B 1/04*     (2006.01)
 *A61B 1/06*     (2006.01)
 *A61B 5/00*     (2006.01)
 *G01J 3/10*     (2006.01)
 *G01N 21/80*    (2006.01)
 *G01J 3/32*     (2006.01)
 *A61B 5/1455*   (2006.01)
 *A61B 3/14*     (2006.01)

(52) U.S. Cl.
 CPC ............. *A61B 3/14* (2013.01); *A61B 5/0071* (2013.01); *A61B 5/14551* (2013.01); *G01J 3/10* (2013.01); *G01J 3/32* (2013.01); *G01J 3/4406* (2013.01); *G01N 21/6428* (2013.01); *G01N 21/80* (2013.01); *G01N 21/91* (2013.01); *G01J 2003/102* (2013.01); *G01J 2003/106* (2013.01); *G01N 2021/6417* (2013.01); *G01N 2021/6439* (2013.01)

(58) Field of Classification Search
 CPC ..... G01N 27/44721; G01N 2021/6417; G01N 2021/6439; G01J 3/4406; G01J 3/10; G01J 3/32; G01J 2003/102; G01J 2003/106; A61B 5/0059; A61B 1/043; A61B 1/0638; A61B 5/0071; A61B 3/14; A61B 5/14551
 USPC ...................................................... 250/459.1
 See application file for complete search history.

(56) References Cited

U.S. PATENT DOCUMENTS

| | | | | |
|---|---|---|---|---|
| 8,849,380 | B2* | 9/2014 | Patwardhan | A61B 5/0059 600/476 |
| 2002/0140933 | A1* | 10/2002 | Oshida | G01N 21/6428 356/317 |
| 2003/0191368 | A1* | 10/2003 | Wang | A61B 1/00009 600/160 |
| 2006/0232776 | A1* | 10/2006 | Hairston | G01J 3/02 356/388 |
| 2008/0062429 | A1* | 3/2008 | Liang | A61B 1/00039 356/497 |
| 2009/0040754 | A1* | 2/2009 | Brukilacchio | A61B 1/0653 362/228 |
| 2009/0042179 | A1* | 2/2009 | Peltie | A61B 1/0638 435/4 |
| 2009/0137908 | A1* | 5/2009 | Patwardhan | A61B 5/0059 600/476 |
| 2009/0323058 | A1* | 12/2009 | Dyba | G01N 21/65 356/301 |
| 2010/0016669 | A1* | 1/2010 | Takaoka | A61B 1/043 600/160 |
| 2010/0056928 | A1* | 3/2010 | Zuzak | A61B 5/0071 600/476 |
| 2010/0157039 | A1* | 6/2010 | Sugai | A61B 1/00009 348/68 |
| 2010/0168586 | A1* | 7/2010 | Hillman | G02B 23/2476 600/476 |
| 2010/0296141 | A1* | 11/2010 | Maruyama | H04N 1/02865 358/509 |
| 2011/0230738 | A1* | 9/2011 | Chance | A61B 5/0059 600/310 |
| 2012/0013722 | A1* | 1/2012 | Wong | A61B 1/00009 348/66 |
| 2012/0085932 | A1 | 4/2012 | Themelis | |
| 2012/0099190 | A1* | 4/2012 | Knebel | G02B 21/002 359/385 |
| 2013/0012794 | A1* | 1/2013 | Zeng | A61B 1/00186 600/328 |
| 2013/0191368 | A1 | 7/2013 | Raichelgauz et al. | |
| 2013/0222562 | A1 | 8/2013 | Ono | |
| 2013/0286176 | A1 | 10/2013 | Westwick et al. | |
| 2013/0296710 | A1* | 11/2013 | Zuzak | A61B 5/0071 600/476 |
| 2013/0302746 | A1* | 11/2013 | Liang | A61B 1/0638 433/29 |
| 2013/0329006 | A1* | 12/2013 | Boles | G06K 7/1413 348/42 |
| 2014/0187967 | A1* | 7/2014 | Wood | A61B 18/20 600/473 |
| 2014/0218726 | A1* | 8/2014 | Cheng | G01N 21/65 356/301 |
| 2015/0051497 | A1* | 2/2015 | Carver | A61B 5/0071 600/476 |
| 2015/0087902 | A1* | 3/2015 | Mertz | G02B 21/14 600/109 |
| 2015/0092035 | A1* | 4/2015 | Yamamoto | G02B 21/06 348/68 |
| 2017/0209050 | A1* | 7/2017 | Fengler | H04N 9/045 |

FOREIGN PATENT DOCUMENTS

| | | |
|---|---|---|
| CN | 101583934 | 11/2009 |
| CN | 102770062 A | 11/2012 |
| JP | 2002-287034 A | 10/2002 |
| JP | 2006-263044 | 3/2005 |
| JP | 2012-189600 | 10/2012 |
| WO | 2009/021079 A1 | 2/2009 |

OTHER PUBLICATIONS

Written Opinion issued in PCT/EP2015/062448; dated Jun. 8, 2016.
Japanese Office Action dated Mar. 6, 2018 issued in corresponding Japanese Patent Application No. 2016-571115 with English translation; 11pp.
Chinese Office Action dated Feb. 2, 2018 issued in corresponding Chinese Patent Application No. 201580042456.7 with English translation; 17pp.
European Office Action dated Oct. 24, 2019 issued in corresponding European Patent Application No. 15 730 081.5-1001; 5pp.

* cited by examiner

METHOD AND MEANS FOR MULTISPECTRAL IMAGING

The present invention relates to the multispectral imaging of samples, in particular of biological tissues.

When imaging tissue the illumination light may be absorbed or scattered. If the tissue contains fluorescent molecules, then the absorbed energy is temporarily stored by setting the molecules at an excited state and then it is released as a photon of longer wavelength. The light intensity from fluorescence is usually many orders of magnitude weaker than the intensity of the reflected excitation light, and it is necessary to separate or block the reflected excitation from the emitted light.

The most practical way is using band-pass filters in the excitation and the emission paths of the beams to limit the spectral range of the lights to avoid the bleed-through of reflected excitation in the recorded emission path. A direct consequence of this method is that it is not possible to acquire the fluorescence image simultaneously with the reflected excitation image in the same detection path.

In order to acquire both the fluorescence and the reflected images it is necessary to switch between the two modes of acquisition: with and without filters. For a static object, i.e. for an object that doesn't move significantly during the acquisition of the fluorescence and reflectance images, it is never a problem to switch between filters and acquire the two images sequentially. However, if the objects in the field of view move, then the recorded images are not coinciding, and registration can be very difficult even after intensive image processing.

Yet, another problem that can arise is the simultaneous imaging of multiple fluorescent agents that have different excitation and emission characteristics. In this case, different sets of imaging filters for excitation and emission must be used to image the different fluorochromes, which eventually increases the complexity and the number of acquired images. Moreover, when imaging moving objects it is necessary to record both the emitted fluorescence and the reflected excitation of an object with rather high video frame rates. Switching between filters must then be accomplished very fast.

There are several approaches that are used to achieve multispectral imaging. They can be roughly characterized by a) the number of sensors used, b) the use of switching filters, c) switching between different illuminations or d) the use of multiple band pass filters, the use of beam splitters, etc. [Y. Garini, I. T. Young, and G. McNamara, "Spectral imaging: Principles and applications," Cytometry Part A 69A, 735-747 (2006)].

These prior art techniques will be described in detail in the following.

[Switching Filters]

Some multispectral imaging systems have a single image sensor and implement a fast switching mechanism between reflectance and fluorescence imaging mode. This can be achieved with use of bandpass excitation and emission filter sets that are mounted on filter wheels or filter cubes that are exchanged fast in order to record reflectance and fluorescence images alternatingly with high frequency. This approach is straightforward and allows the highest throughput of light, but requires mechanically moving parts like filter wheels. Further, depending on the filter configuration, it allows the recording of the intensity of only one fluorophore at a time. Switching filters at near video rate frequencies is technically complex and requires accurate mechanical synchronization with the frame grabbing sequence of the camera.

To avoid mechanical components one may use spectrally tunable filters, for example liquid crystal tunable filters. The switching between spectral settings suitable for different fluorophores can be very fast (<1 ms), however the transmission throughput of the tunable filters is limited. Furthermore, they are highly sensitive to light transmission angles and light polarization, and are associated with rather high costs.

[Beam Splitters]

An alternative approach for multispectral imaging is to use multiple sensors, where in front of each sensor a corresponding emission filter is arranged. The light can reach each sensor either by passing through a single objective lens and using an optical beam-splitter arrangement to deliver the light to each sensor, or each sensor can have a separate objective lens. In any case, each sensor is paired with a filter that can block the excitation wavelengths and record the emission from one fluorophore [Lucia M. A. Crane et al., et al. J Vis Exp. 2010; (44): 2225.]. An additional sensor can record the reflection image with a different imaging path. This concept is simple, but the use of multiple sensors, beam splitters or objective lenses increases the size, the complexity of design and the cost.

[Fast Switching Illumination]

Another solution for multispectral imaging uses switching between different excitation lights. Therein, the object is alternatively illuminated with excitation beams that have a specific excitation spectrum that is blocked by filters to enter into one or more cameras. In US 20130286176 A1 a single color sensor, a laser excitation to excite fluorescence, and a broadband illumination source that switches on and oft is used. When only the laser excitation source is on, then the sensor can capture the emitted fluorescence, and when the broadband illumination is on, then the sensor can capture the reflected image. This system produces a reflectance image and an image of a fluorochrome, but an observer might visually experience a disturbing flickering due to the on-off switching of the different sources.

[Blocking Multiple Bandpass Images]

Yet another approach uses filters with multiple-band pass regions paired with a monochrome sensor. In this approach a filter in front of a monochrome sensor blocks the excitation wavelengths to enter into the monochrome sensor. The different fluorophores can be imaged individually with excitation scanning. Alternatively the filtered multi-component fluorescent light can be split into wavelength dependent paths which are then imaged onto different spatial regions of a monochrome sensor. With this approach it is possible to record multiple channels simultaneously with a monochrome sensor.

In an alternative approach a color sensors can be used to record the multi-component fluorescent light with a multi-channel (and thus color) sensor. The multi-channel sensor output can then be processed in order to obtain the individual fluorescent components.

An additional sensor can be used to record the reflectance image by splitting the reflected excitation light into a different optical path imaging that light on that sensor. This offers multiple fluorescence imaging bands together with the reflectance, but an observer will visually perceive false color representation. Depending on the specific excitation wavelengths, the false perception might not be possible to be corrected even digitally.

It is possible to further split both, the reflectance and the fluorescence onto multiple additional color sensors to increase the number of spectral channels. Each channel has a narrow bandpass filter in front of the sensor and the intensity in each individual narrow filter band is computed [US 20120085932 A1].

The used filter sets are known as "Pinkel", "Sedat", or "Full-multiband" depending on the exact combination of excitation and emission filters used in the specific application.

The present invention is made to provide a method and means for multispectral imaging, which avoid the above mentioned problems of the prior art and are simple, quick and costeffective.

This problem is solved by the method according to claim 1 and the apparatus according to claim 12 as well as the endoscope or surcical microscope according to claim 17 and their uses according to claim 18.

In the following different examples of the present invention are provided. Therein, for similar or same elements similar or same reference numbers are used. In the following examples a combination of features which are essential and optional for the present invention may be described in combination. However, each of the optional features described in such a combination may be used separately and singly to improve the invention as described in the present claims.

Figure 1:
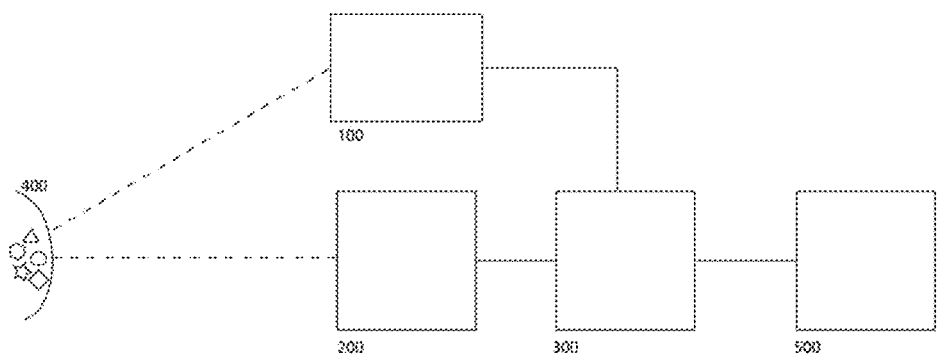
FIG. 1 shows a general apparatus according to the invention.
Figure 58:
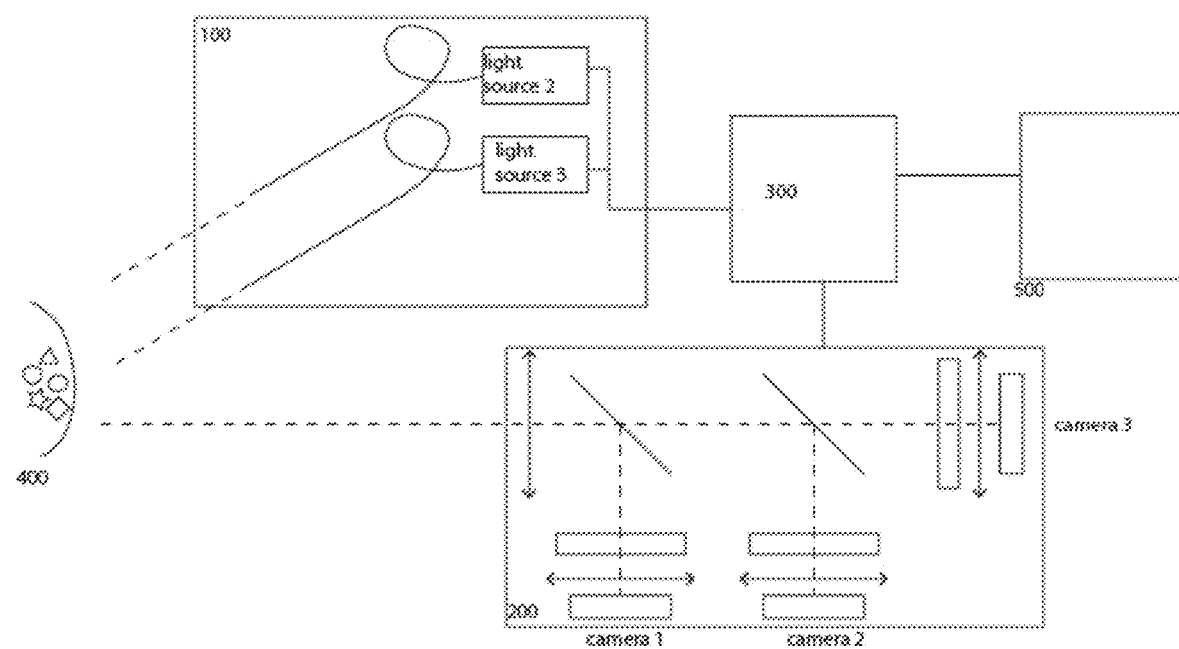
FIG. 58 shows an apparatus according to the invention.

Examples are shown in combination with FIGS. 1 to 58, which all show aspects of inventive examples.

EXAMPLE 1

FIG. 1 describes the general concept of the invention. The inventive system comprises an illumination system 100 that produces and guides light that incorporates spectral and time multiplexing properties to illuminate an object 400. The light emanating from the object 400 is collected and detected or imaged by an imaging system 200 that is comprised of elements like lenses, filters, beam splitters, and light sensor/detector arrays (i.e. cameras), etc. Both the illumination system 100 and the detection system 200 are connected to a controlling and processing unit 300 that controls the operation of the illumination system, synchronizes the operation and grabs the images from the detection system 200, and processes the image data, for further evaluation, display and storage. Finally, a display/visualization system (500) displays the decomposed images either separately or simultaneously/in overlay.

Figure 2:
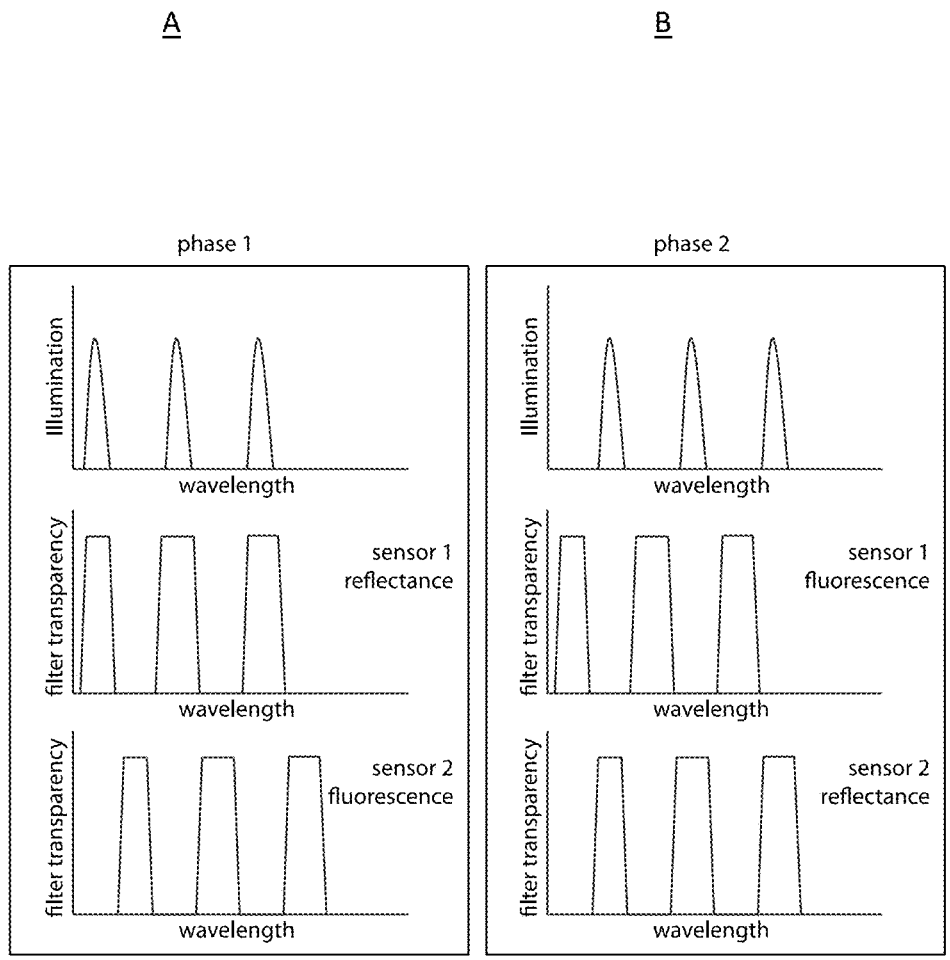
FIGS. 2A and 2B show illumination light spectra and filter transmission spectra.

The illumination system 100 operates in two (or more) alternating phases as shown in FIG. 2. In the phase 1, the system illuminates the object with light exhibiting a spectral shape with areas of high and low intensities similar to that depicted in FIG. 2A. In FIG. 2A and FIG. 2B for each illumination phase, the spectrum of illumination and the transmission spectra in front of the two sensor arrays are provided. Various spectral shapes are possible, but it is essential that the light has spectral regions with very low intensity at wavelengths longer than the high intensity regions. In those regions fluorescent light emitted by the object upon excitation with the first light can be detected by the imaging system without detecting relevant amounts of reflected light. In phase 2 of illumination the object is illuminated in general with a light that has a different spectral shape, and is preferably exhibiting an approximately complementary structure as shown in FIG. 2B. The imaging system 200 comprises of two (or more) imaging channels/paths split by a beam splitter 202 or an equivalent method. Each imaging channel has image sensor arrays 211, 221 to detect and record fluorescence and reflectance images at the different phases. The light reaching the image sensors is spectrally attenuated so that in general the illumination light of phase 1 is attenuated before reaching the imaging sensor 2 and the illumination light of phase 2 is attenuated before reaching the imaging sensor 1.

|  | Sensor array 1 | Sensor array 2 |
| --- | --- | --- |
| Illumination phase 1 | Reflectance | Fluorescence |
| Illumination phase 2 | Fluorescence | Reflectance |

By alternating the illumination of the object it is possible to alternatively record spectrally complementary reflectance and fluorescence images with the two sensors. In illumination phase 1 the spectral bands of the light reflected from the object are transmitted and detected into detector sensor 221 forming a reflectance image, whereas the fluorescence emission from the object is transmitted and detected into sensor 211 forming a fluorescence image. In illumination phase 2 the spectral bands of the light reflected from the object are transmitted and detected in detector sensor 211 forming a reflectance image, whereas the fluorescence emission from the object is transmitted to and detected in sensor 221 forming a fluorescence image.

The amount of attenuation before the light reaches each sensor can be approximately estimated such that when a sensor is preferably used to detect fluorescence (i.e. sensor 221 in phase 2, and sensor 211 in phase one) the detected fluorescence signal should preferably be 100 times more than the bleed through of the excitation light.

EXAMPLE 2

Figure 3:
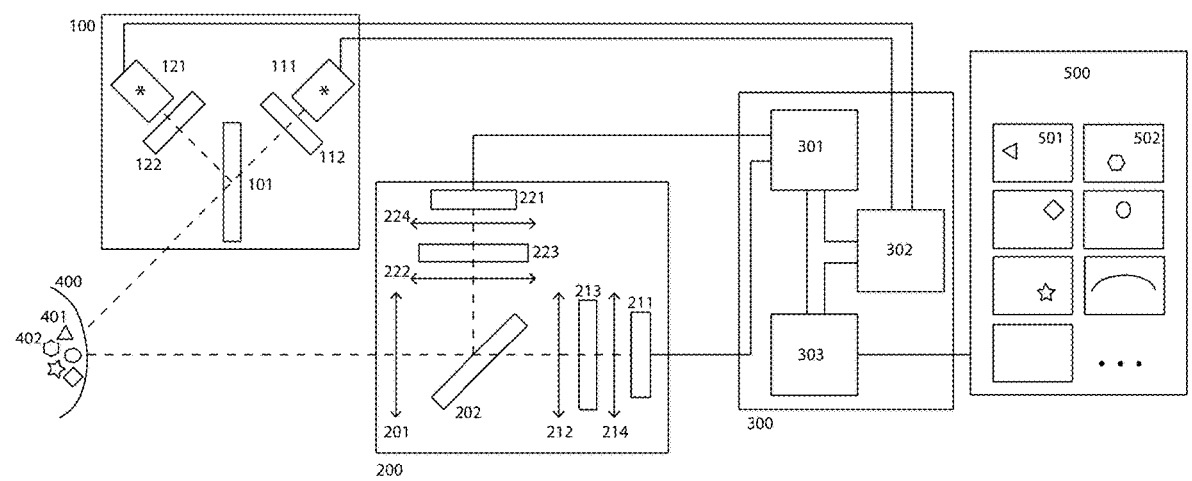
FIG. 3 shows a preferred embodiment of the invention.

One of the preferred embodiments is shown in FIG. 3. It uses two broadband white light sources 111 and 121, which can be switched on and off alternatively, filtered by two complementary multiple bandpass filters 112 and 122. The two beams from these two light sources 111 and 121 are combined with a multiple bandpass polychroic mirror 101. In between those elements, collimation lenses may optionally be placed in order to guide more light to area to be imaged. The imaging system 200 consists of lenses, filters, mirrors, and imaging sensors. The light coming from the object 400 is collected in the detection system 200 with an objective lens 201 (or a system of lenses acting as an objective lens), which for use in open surgeries preferably has a focusing distance of 200 mm. The light after the objective lens is splitted by a multichroic bandpass mirror 202 and splits the light into two paths that these light paths have complementary spectral content. Two complementary multiple bandpass filters 213 and 223 attenuate the beams that are imaged by a multi-channel or multi-color sensor arrays 211 and 221. The processing/controlling unit is consisted of a frame grabber 301, a controlling unit 302, and a processing unit 303, to generate images 501, . . . 507. Optional lenses 212, 214, 222, 224 can be used in between the various elements to relay the image to the sensor. The mirror beam splitter (202) and the multi-bandpass filters 213 and 223 are preferably placed in an optically infinity corrected imaging space. The mirror 202 is usually 1-3 mm thick. In order to maintain the optical imaging quality, the flatness of the dichroic mirror 202 should be λ/10.

Figure 4:
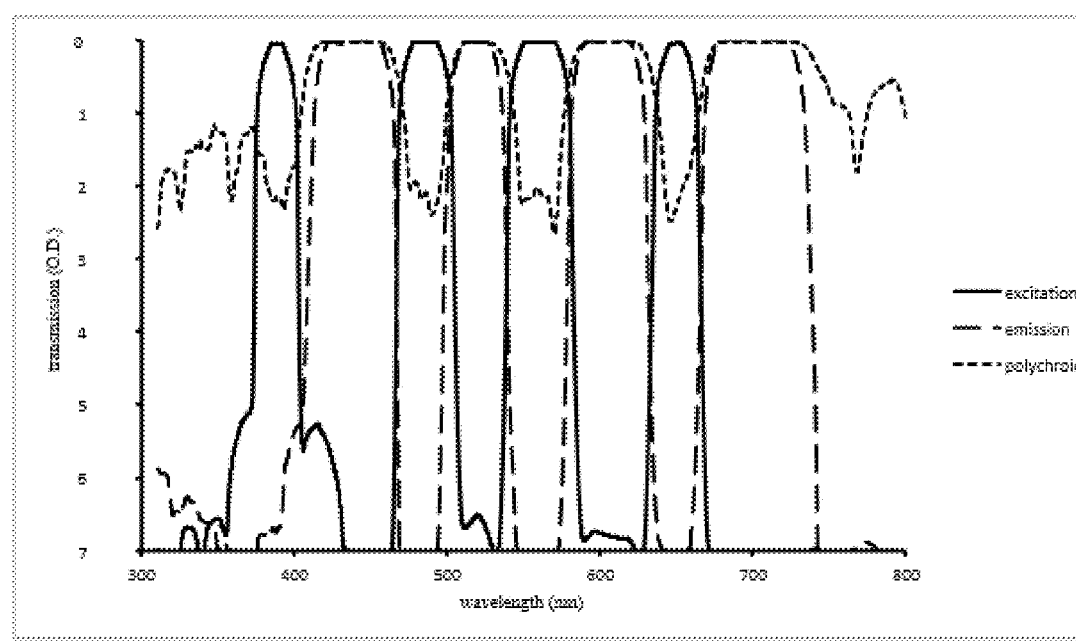
FIG. 4 shows the transmission spectrum, of a four band filter set.

Interference multiple bandpass filters and polychroic filters are usually manufactured as excitation/emission/mirror filter sets for use in fluorescence microscopy as Sedat, Pinkel or full multiband sets. An example of a four-band filter set which is originally configured for imaging four fluorochromes is shown in FIG. 4. This set can be configured to be used both in the illumination and imaging system. The excitation filter can be used in positions 122 and 223, the emission filter in positions 112 and 213, and the polychroic mirror in (101) and (202). Various different combinations of filters, filter sets may be optimized for various fluorochrome applications. Preferably there is a small spectral gap provided between the filter transmission bands to avoid crosstalk (see schematics). The width of that band depends on the characteristics of the filter to operate under a range of angles of incidence combined with the requirement of the filter set to perform in an environment with realistic conditions.

Using such a filter set for the two illumination modes means that in phase 1 the excitation filter of the set is used to filter white light from source 121 and in phase 2 the emission filter is used to filter white light from source 111. The polychroic mirror 101 is used to combine the beams in one. In practical terms and assuming nominal concentrations of fluorochromes in tissue (usually between $100 \times 10^{-9}$ M to $1 \times 10^{-3}$ M) the usual attenuation ratio in the rejection bands of interference multiple bandpass filters of optical density (O.D.) of 6 orders of magnitude is sufficient, however it is expected that in many cases attenuation of 2 or 3 O.D. can be adequate.

Figure 5:
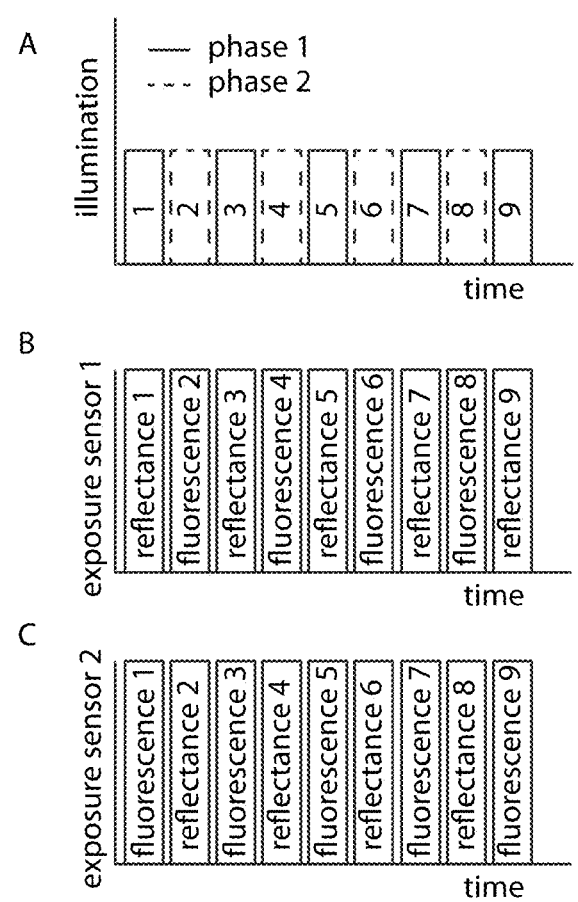
FIGS. 5A, 5B and 5C show the phase sequence of illumination and recording in an embodiment of the invention.

As shown in FIG. 5A, phase 1, the object 400 is illuminated with spectrally shaped light that is partially reflected, transmitted, and absorbed to excite fluorescence. The reflected excitation light in phase 1 is attenuated by the emission filter 213 in front of sensor 211, which records only the fluorescence emission. Complementary, the filter 223 in front of sensor 221 transmits the reflected excitation light, so the 221 sensor detects the reflected excitation light in phase 1. In contrast, in phase 2 the object 400 is illuminated with light, which has an approximately complementary spectral shape to the illumination light in phase 1. The illumination light in phase 2 is partially reflected, transmitted and absorbed by the object to also excite fluorescence. The excitation light reflected from the object is transmitted by the filter 213 and detected by the sensor 211, which detects a reflectance image of the object. Complementary, the filter 223 in front of sensor 221 attenuates the reflected excitation coming from the illumination source in phase 2 and records the fluorescence emission. To summarize, in phase 1, sensor 211 is recording fluorescence and sensor 221 is recording reflectance images of the object 400. In phase 2, sensor 221 is recording fluorescence and sensor 211 is recording fluorescence images of the object 400.

A series of sequentially acquired reflectance and fluorescence images is shown in FIGS. 5B and C. The system can image both fluorescence and reflectance images of (almost) the entire visible spectrum. This means that in every two illumination cycles (phases) the reflectance and the fluorescence images are complementary recorded without missing any relevant or substantial part of all spectral regions. If the frequency of illumination phases and recording of the images is fast enough to accommodate any possible object movement, by combining the reflectance image of each frame with the reflectance image of the previous frame from the opposite sensor, which has a complementary reflectance spectrum, a composed reflectance image of the whole spectrum is created. That is combining the Reflectance 1 with Reflectance 2, Reflectance 2 with Reflectance 3, and so on. Similarly, combining the fluorescence image of each frame with the fluorescence image of the previous frame from the opposite sensor, which has the complementary fluorescence spectrum, a composed fluorescence image of the whole spectrum is created. That is combining the Fluorescence 1 with fluorescence 2, Fluorescence 2 with Fluorescence 3, and so on.

This combination method not only increases the spectral coverage of both fluorescence and reflectance but also multiplies the number of spectral measurements per camera. Thus this technique offers surplus spectral imaging (for comparably small changes). Only few small spectral regions will not be recorded due to a practical implementation problem that a small spectral gap may be necessary to exist between complementary spectral areas. Though, those spectral gaps do not alter the color impression of the image.

The controlling of the illumination of the object and the exposure of the sensors is provided from signals in the processing and controlling unit 300. The two broadband light sources can be incandescent lamps, gas lamps (like Hg, Xe, or mixtures), light emitting diodes (LEDs), or any other broadband light source. LED sources can be switched on and off at a high frequency rate, with rise and fall times faster than 100 microseconds. The system can illuminate the object with alternating phases at video rate, i.e. approximately at 25 fps. At this and at higher illumination rates the visual perception of the illumination field is uniform, where any flickering effect is hardly observable. Additionally, since the two phases have complementary spectral illumination the overall color balance of the system is of a broadband white color, similar to the color appearance of the light of each of the broadband sources without filtering.

Figure 6:
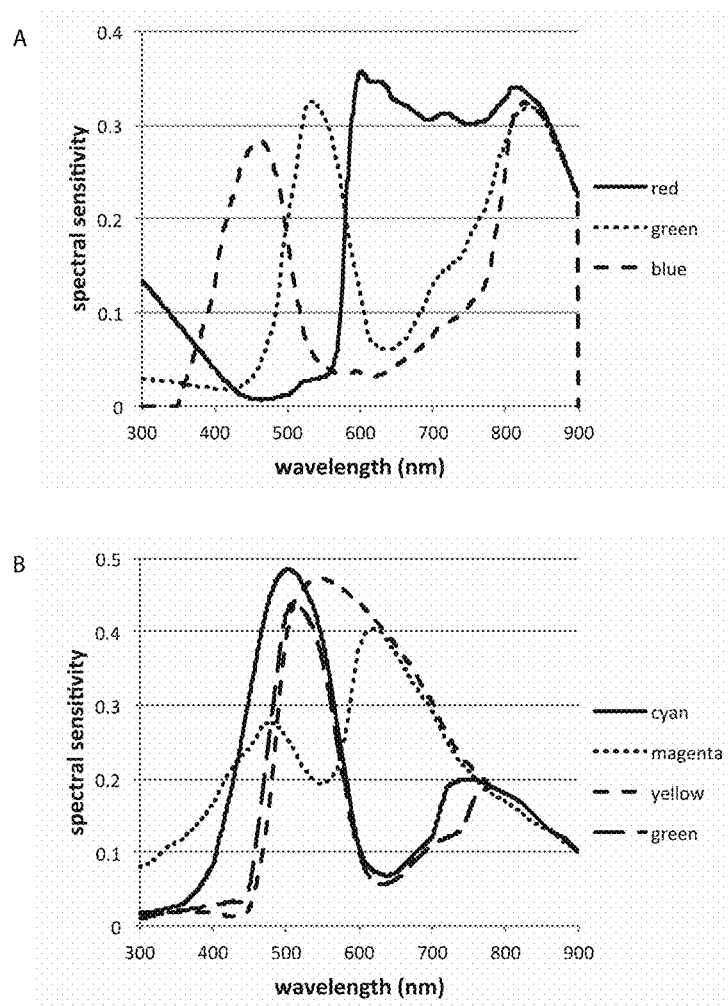
FIGS. 6A and 6B show color sensitivies of sensor array used in an embodiment of the invention.

The sensor is preferably a multi-channel (multi color) sensor that has the capability to record the images in multiple spectral areas. Each spectral area has a distinct spectral sensitivity and records the reflected light of a spectral multiplex of various reflecting and fluorescence substances in the object. Examples of a multichannel color sensors arrays are the RGB (red-green-blue) or the CMYG (cyan-magenta-yellow-green) pattern sensors and typical color sensitivities are shown in FIG. 6. These signals are spectrally mixed and are spectrally unmixed by image processing.

EXAMPLE 3

Images that are acquired are transferred to the processing unit 300 for a series of image processing operations, such as demonstrating, registration, noise filtering, background dark noise subtraction, color correction for the color frames, and spectral unmixing. In particular the spectral unmixing in the simplest form can be a linear transformation between the color channel images generated from the camera and the component space. Components can be anything that the light can carry information from, such as materials, concentrations or properties, or quantities that can be derivatives from those components and they may have a particular spatial distribution similar to the parts 401, 402 of the object 400, and so on. After the calculation of the images of the spatial distribution of the components 501, 502, and so on, they can be stored, displayed, or overlaid on other images, with the use of colormaps, such as pseudocolor.

Some examples, but not limited to this are: a) Absorber distribution. The spectrum of the reflected light is shaped by the absorption and transmission spectrum in tissue, and this is recorded in the color sensor signals. By system and tissue modeling tissue absorption and/or system calibration on absorbers with known concentrations, it is possible to derive the concentration of intrinsic tissue absorbers like oxygenated and deoxygenated hemoglobin, melanin, etc. or also externally administered absorption contrast agents e.g. methylene blue. b) Additionally, from the maps of the oxygenated and deoxygenated hemoglobin distribution it is possible to calculate an oxygen saturation map, and relevant physiological or pathological parameters c) Fluorochrome distribution. Fluorescence comes either from endogenous fluorochromes or externally administered fluorescent contrast agents. The fluorescence signals are recorded by the color sensor and by system and tissue modeling and/or system calibration it is possible to derive the fluorochrome distribution. Additionally, it is possible to calculate ratios between fluorochrome maps, which convey more specific information on cancer.

EXAMPLE 4

In the following a basic description for exemplary image processing for the calculating the fluorescence components is presented. Similar values like reflectance absorption distribution, and derivative values are modeled and calculated similarly. The camera measures the signal intensity of different color channels. This signal is created by the light intensity of the sum of all components, which are spectrally filtered by the transmission filters and additionally by the RGB color filters combined with the spectral sensitivity of the sensor. Assuming that the detector response is linear, the signal generated is:

$$S_{c\in\{color\}} = \int_{\lambda_{min}=0}^{\lambda_{max}=\infty} \sum_{f\in\{fluorescenct\ channels\}} I_\lambda(\lambda, f) * T(\lambda, c)d\lambda \quad \forall\ c\in\{color\}$$

where $S_c$ is the signal in a specific spectral color c out of all combined color sensor images; for example {color}={R1, G1, B1, R2, G2, B2 ... }. $I_\lambda(\lambda, f)$ is the spectral fluorescence channel intensity density. It depends on the wavelength and the fluorescence channel. Each fluorescence channel is characterized by a specific spectral light characteristic. In the simplest case the spectral light characteristic of a fluorescence channel of the imaging system corresponds to a fluorophore. In this case the $I_\lambda(\lambda, f)$ corresponds to the spectral emission spectrum of the fluorophore. In this case exact value of $I_\lambda(\lambda, f)$ can be determined considering the fluorophore concentration, the fluorophores quantum yield and the spectral illumination light intensity. $T(\lambda, c)$ is the total transmission characteristics of the specific spatial color sensor or pixel which also exhibits the transmission characteristics of the optical system including the emission filter. Assuming that the fluorescence activity is located close to the tissue surface so that the fluorescence emission spectral profile and intensity are not strongly influenced by the tissue intrinsic absorption, and that other non-linear effects like quenching are negligible, then the spectral fluorophore intensity $I_\lambda(\lambda, f)$ can be written as $I_\lambda(\lambda, f) = c(f) * \Phi_\lambda(\lambda, f)$:

$$S_{c\in\{color\}} = \int_{\lambda_{min}=0}^{\lambda_{max}=\infty} \sum_{f\in\{fluorescenct\ channels\}} c(f) * \Phi_\lambda(\lambda, f) * T(\lambda, c)d\lambda \quad \forall\ c\in\{color\}$$

where c(f) is the concentration of fluorophore f. In case the fluorescence channel f is used for reflectance imaging, c(f) is the intensity factor. Symbol for the concentration c is the same as the color channel index. $\Phi_\lambda(\lambda, f)$ is the molar spectral fluorescence intensity density describes the spectral profile of the emission of a fluorophore f. The intensity is scaled by the concentration of the fluorophore c(f). In case f is a reflectance channel, $\Phi_\lambda(\lambda, f)$ is the normalized spectral reflectance intensity of a channel with a spectral distribution. As one example, $\Phi_\lambda(\lambda, f)$ could be the spectral response of the red receptor in the eye. This would lead to a natural color impression for this red channel. After rearranging the formulation $$S_{c\in\{color\}} = \sum_{f\in\{fluorescenct\ channels\}} c(f) * \underbrace{\int_{\lambda_{min}=0}^{\lambda_{max}=\infty} \Phi_\lambda(\lambda, f) * T(\lambda, c)d\lambda}_{M(f,c)} \quad \forall\ c\in\{color\}$$

leads to the linear relation between fluorophore concentration and measured channel intensity of the sensor:

$$S_{c\in\{color\}} = \sum_{f\in\{fluorescenct\ channels\}} c(f) * M(f, c) \quad \forall\ c\in\{color\}$$

Figure 7:
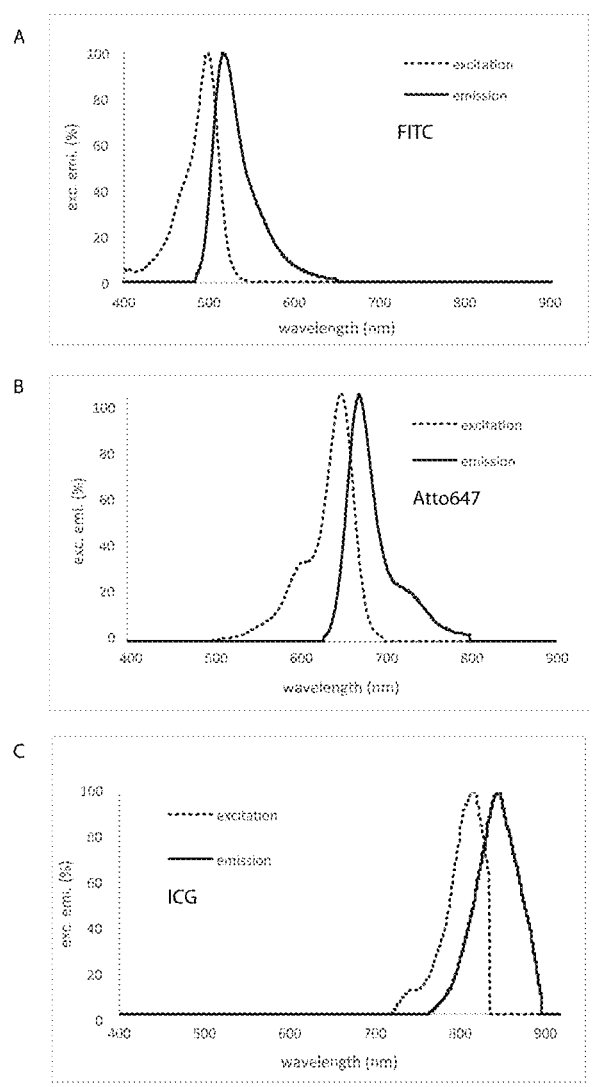
FIGS. 7A, 7B and 7C show excitation and emission spectra of several fluorophores.

This linear relation allows computing all fluorescent and reflectance channel intensities c(f). Herein, there is an example of the calculation of the matrix M for a sensor with the channels red, green and blue and the dyes fluorescein isothiocyanate (FITC), Atto647 and Indocyanine green (ICG). Their fluorophore excitation and emission spectra are given in FIG. 7.

The signal equations are:

$$S_{red} = c(FITC) * M(FITC, red) +$$
$$c(Atto647) * M(Atto647, red) + c(ICG) * M(ICG, red)$$

$$\begin{pmatrix} S_{red} \\ S_{green} \\ S_{blue} \end{pmatrix} = \begin{pmatrix} M(FITC, red) & M(Atto647, red) & M(ICG, red) \\ M(FITC, green) & M(Atto647, green) & M(ICG, green) \\ M(FITC, blue) & M(Atto647, blue) & M(ICG, blue) \end{pmatrix} * \begin{pmatrix} c(FITC) \\ c(Atto647) \\ c(ICG) \end{pmatrix}$$

With the coefficients M exemplary written for the combination of FITC and the red detector channel:

$$M(FITC, red) = \int_{\lambda_{min}=0}^{\lambda_{max}=\infty} \Phi_\lambda(\lambda, FITC) * T(\lambda, red)d\lambda$$

The fluorescence intensities can be obtained by inverting the coefficient matrix M:

$$\begin{pmatrix} c(FITC) \\ c(Atto647) \\ c(ICG) \end{pmatrix} = M^{-1} * \begin{pmatrix} S_{red} \\ S_{green} \\ S_{blue} \end{pmatrix}$$

If the number of detector color channels is equal to the number of fluorescent channels to be resolved, the equation system can be solved as a linear system of equations. The variables $S_c$ are measured by the imaging system. The values of c(f) can be calculated if the other parameters of the system are known ($\Phi_\lambda(\lambda, f)$ and $T(\lambda, c)$). These factors and therefore the matrix M(f, c) can be determined in advance in a calibration process. In order to calculate c(f) the matrix M(f, c) needs to be inverted.

If the number of measured channels is larger than the number of fluorescence channels, the system is over-determined. One option to handle this favorable situation is to compute the pseudo-inverse of M(f, c) which is not anymore a square matrix. Various algorithms may be used to improve the outcome of the calculation and for example minimize noise originating from the measurements in the sensors.

The matrix M can be either calculated from system modeling and/or from system calibration. In system modeling, the light path spectral content can be modeled from the light source to the color sensor array pixels. Parameters include but are not limited to illumination source spectral distribution, the spectral transmission of the excitation filters, or the spectral profile of the illumination lights, the fluorochrome, excitation and emission spectra and the quantum yield, possibly the approximate depth of the components in tissue, also as the optical properties of tissue, the transmission characteristics of the imaging system (lenses, beam splitters, filters, mirrors, etc.) and finally the spectral sensitivities of the sensor array. The modeling calculates the matrix M that connects the concentration information to the recorded signals (forward problem) and the component distribution can be derived from the solution of the inverse problem. Alternatively, system calibration can be done with either recording the signals of components of known composition, concentration and location, and then solving for the unknown matrix M, or by a blind decomposition with unmixing algorithms, such as Principle Component Analysis (PCA), Independent Component Analysis (ICA), or similar statistical algorithms. Finally, modeling, or in general the use of prior information, can potentially be used to determine more unknowns than the number of measured channels.

Alternatively to the linear modeling description the system can be modeled in more detail using a non-linear description. In this way it is possible to take into account the potential of non-linearities, such as the detector or the quenching effect of high fluorochrome concentrations. Finally, with modeling and/or prior information it is possible to calculate a matrix that recovers the information from components that are more than the available channels, in what would originally be an underdetermined system.

Finally, as described before, the number of components unmixed is related to the total number of channels (colors) available from the combined images from the color sensors. However, the number of spectral bands in the illumination and/or the transmission is independent from the number of channels (colors) and the number of components unmixed. In general the more bands available in the region of interest, the less likely is that a spectral feature from a particular component will not be recorded. Thus, many "narrow" spectral bands offer more accurate color representation of the reflectance image, and more accurate unmixing of the various components. Yet, spectral unmixing of various components is feasible with a number of spectral bands that is smaller than the number of channels.

It is important to highlight, that the number of spectral bands of multiband filters is not a relevant mathematical condition for the number of fluorophores to be unmixed. Instead the number of camera channels is the mathematically important condition.

EXAMPLE 5

In the following the basic light source and various alternatives are described.

[Basic Light Source]

Figure 8:
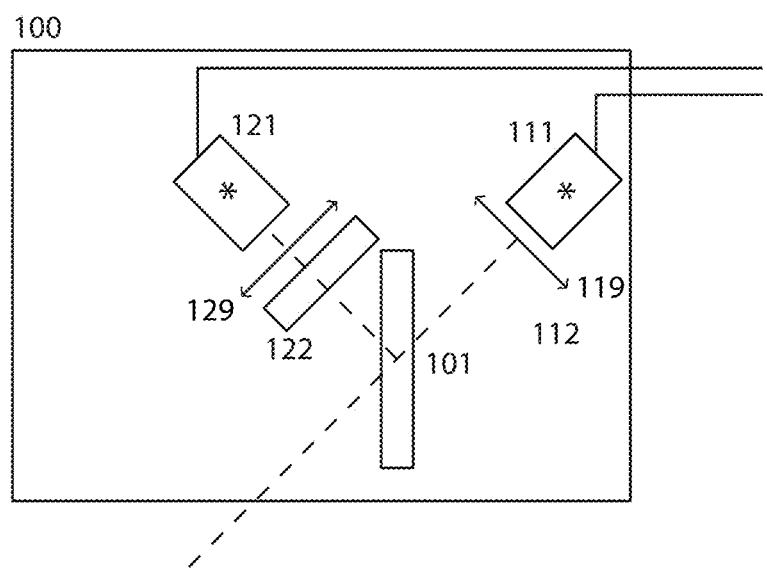
FIG. 8 shows a light source used in an embodiment of the invention.

As previously described the most basic light source 100 (see FIG. 8) consists of two separate light sources 111, 121, which are preferably broadband LEDs 111 and 121. LEDs generally have very fast switching performance compared to conventional light sources such as Halogen or Xenon lamps. The beams are optionally collimated with a collimation lens 119 and 129, and the source 121 is filtered with filter 122 and then combined using a polychroic mirror 101.

FIG. 9A shows the spectrum of the broadband LEDs, that can be the same or different for light source 111, 121. The spectrum is typical for a white light LED. FIG. 9B shows the transmission spectrum of the multi-band excitation filter 122. FIG. 9C provides an intensity spectrum of the light emitted by LED source 121 and filtered by filter 122.

In a preferable embodiment the emission spectrum of the two broadband high power LED sources with a maximum spectral power density is more than 30 mW/nm. This light is filtered with a multi-bandpass filter as shown in FIG. 9B. The filter has transmission bands (420-460 nm, 510.5-531.5 nm, 590-624 nm, 677.5-722.5 nm) with an approximate maximum transmission of 90% in each transmission band. The attenuation characteristics of the filter in the blocking regions are typically at least of optical density 2 (O.D. 2). Usually the out of band rejection/attenuation characteristics of the filters are as good as O.D. 6.

Figure 9:
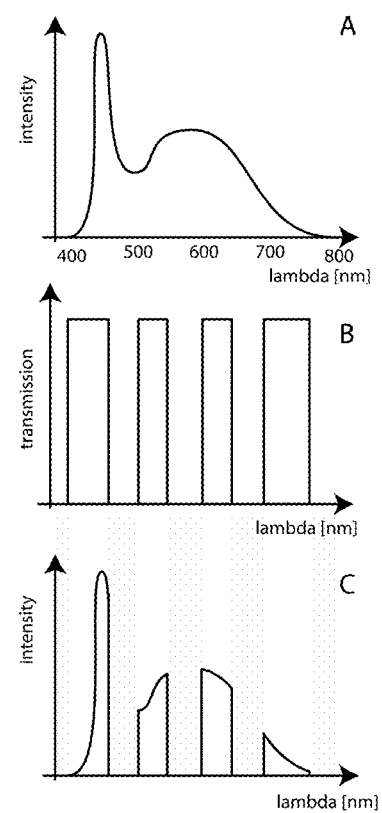
FIGS. 9A, 9B and 9C show an emission spectrum of a light source, a transmission spectrum of a filter, and the emission spectrum of the light source after filtering with the filter.

The effective emission of the light source after filtering with the respective multi-band filter is illustrated in FIG. 9C. The spectrum of the first light (source) is shaped by the accumulated light during this illumination phase and the spectrum of the second light (source) is the intrinsic broadband emission profile such as in FIG. 9. A or similar broadband. Thus all the drawn spectra of light are accumulated spectra during the respective phase.

One potential disadvantage with this basic light source is that the illumination field might not be optimal for the visual perception of an observer both in terms of intensity and of spectral content. The two lights have different overall intensity and spectral content and when they are alternating may present a visual flickering of intensity or color. Additionally the spectral content is not balanced and the color appearance may not be natural.

[Light Source with Two Filters]

Figure 10:
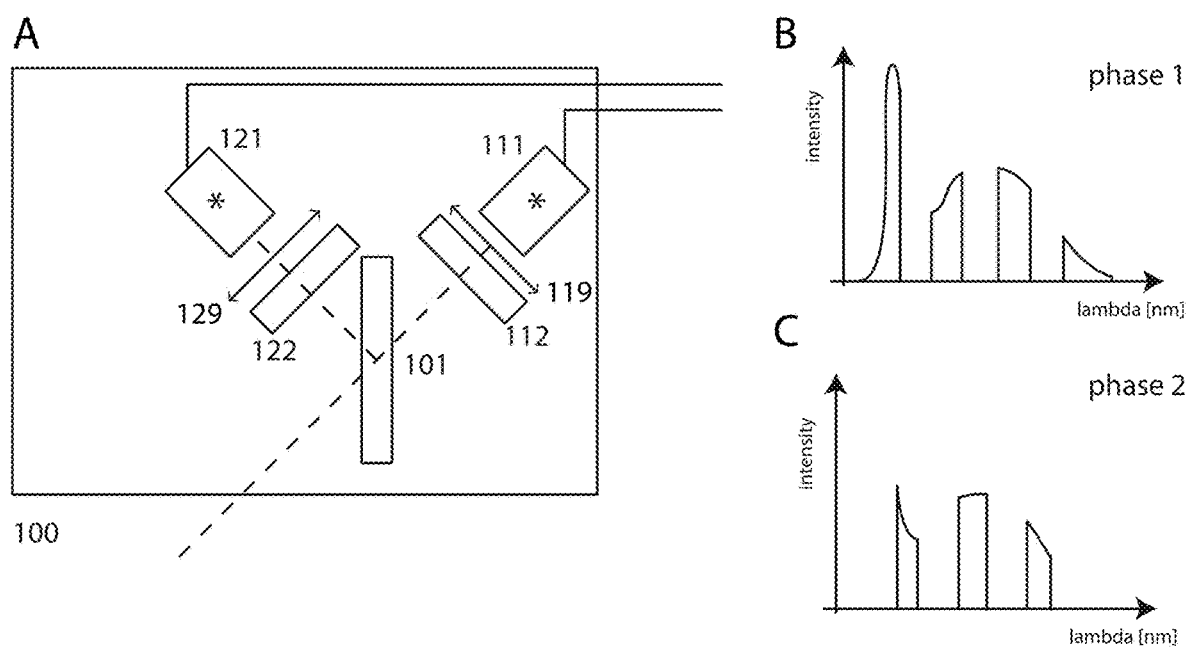
FIGS. 10A, 10B and 10C show a light source used in an embodiment of the invention and its emission spectrum after filtering with various filters.

An alternative illumination source is a variation of the basic light source, with the difference being that the second light is also filtered with a filter 112 (FIG. 10). The basic advantage of filtering the second light is that it facilitates the optimization of the overall color perception and minimizes the flickering. The filter 112 may also be a multiple bandpass filter. Its spectral transmission characteristics may be complementary to the filter 122 and may have the same or similar transmission characteristics to the fluorescence emission filter 213 in front of the sensor array 211 (see FIG. 10B and FIG. 10C). The complementary filters 112 and 122 accumulatively provide a spectrally continuous illumination that is almost equal to the broadband illumination of the original broadband source thus providing natural color perception. Additionally the effect of intensity or color flickering is less. Nevertheless, the spectral shape of the light illumination of the second light (phase 2) is free to modify in order to achieve optimum color perception and minimal intensity flickering.

[Fiber Coupled Light Source]

Additionally the output of the light source 100 can be coupled with a fiber coupling lens system into a light guide. This light guide can either be a single optical fiber, a fiber bundle, or a liquid light guide.

[Light Source with Individually Controlled Narrow Band Sources]

Figure 11:
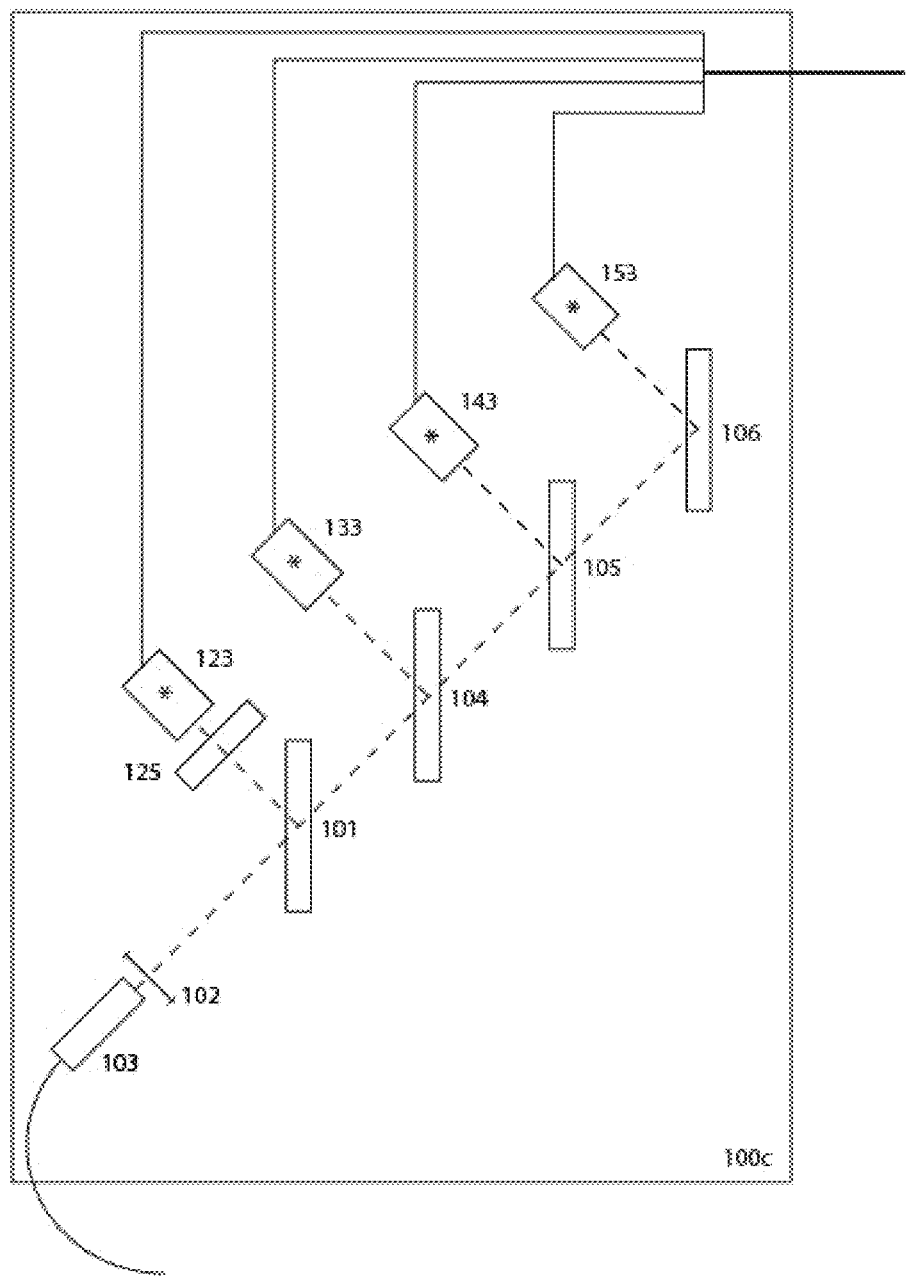
FIG. 11 shows a light source used in an embodiment of the invention.

In an alternative implementation of an illumination system one or more of the broadband light sources that are filtered with the multiband filters is replaced with a set of narrowband individually controlled sources optionally filtered by respective narrow band filters. Such sources can be lasers, laser diodes, LEDs, etc. A basic schematic is shown in FIG. 11. where the light emitting module 111 has been replaced by multiple laser sources 123, 133, 143, 153. The emitted light of the module 123 is filtered by the filter 125. The polychroic mirror 101 combines the radiation of the lasers with the radiation of the module 123. All the lights is coupled together to the fiber 103.

The beam splitter 101 may also be a polarization beam splitter. In this way the different sources at the same wavelength can be combined minimizing the losses. Multiple lasers 133, 143 and 153 may replace one broadband source, e.g source 111 in FIG. 10. The lasers may have a thin spectral emission profile or might also be tunable. Some lasers may require a cleanup filter to suppress unwanted amplified spontaneous emission. The lasers may also be tunable in wavelength and intensity, they may be continuous wave or pulsed. The different laser sources are combined by longpass polychroic mirrors 104 (cutoff wavelength) 415 nm, 105 (cutoff wavelength 650 nm) and 106 (plain mirror with high reflectivity around 785 nm) These, or similar, narrowband sources comprising the illumination in one phase may illuminate simultaneously, with full or partial time overlap, or may operate sequentially. Nevertheless, any time combination within the exposure period associated with an illumination phase is considered as an accumulative light spectral distribution in one illumination phase.

Figure 12:
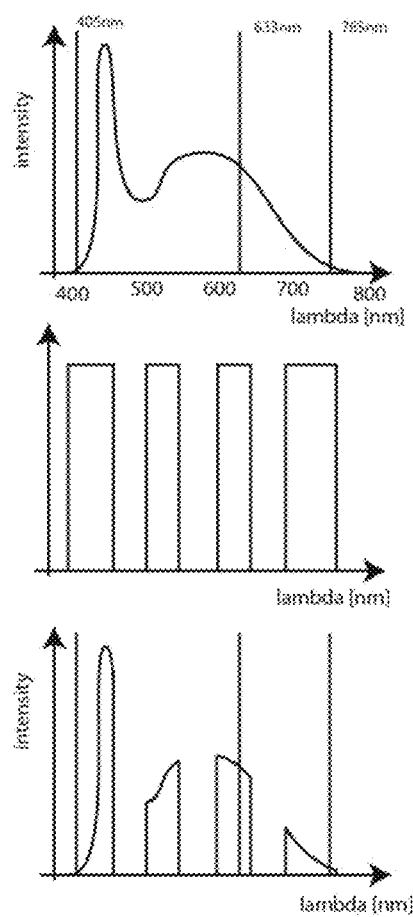
FIG. 12 shows a emission spectrum of a light source used in an embodiment of the invention, a transmission spectrum of a filter and the emission spectrum of the light source after filtering with the filter.

A preferred spectral scenario is illustrated in FIG. 12. FIG. 12 shows the spectrum of the first light source shown in FIG. 11. The upper graph shows the individual spectral intensities of the broadband LED light source and the intensity of the individual narrowband lasers. The middle graph shows the transmission spectrum of the emission filter. The lower image shows the combined intensity of the light which is coupled into the optical fiber. Therein a broadband LED source covers the entire spectral range and is combined with narrowband laser sources which are may preferably be (for switching reasons) laser diodes. In this case popular modules like the 405 nm, the 633 nm and the 785 nm laser diode modules are used. The diode laser at 405 nm can excite protoporphyrin IX (PPIX) which is widely used for brain surgery. The diode laser at 633 nm can excite a highly stable and bright fluorophore such as Alexa647 used in fluorescent probes, and the diode laser emitting at 785 nm excites the clinically relevant indocyanine green (ICG).

[Multiple LED Sources]

Figure 13:
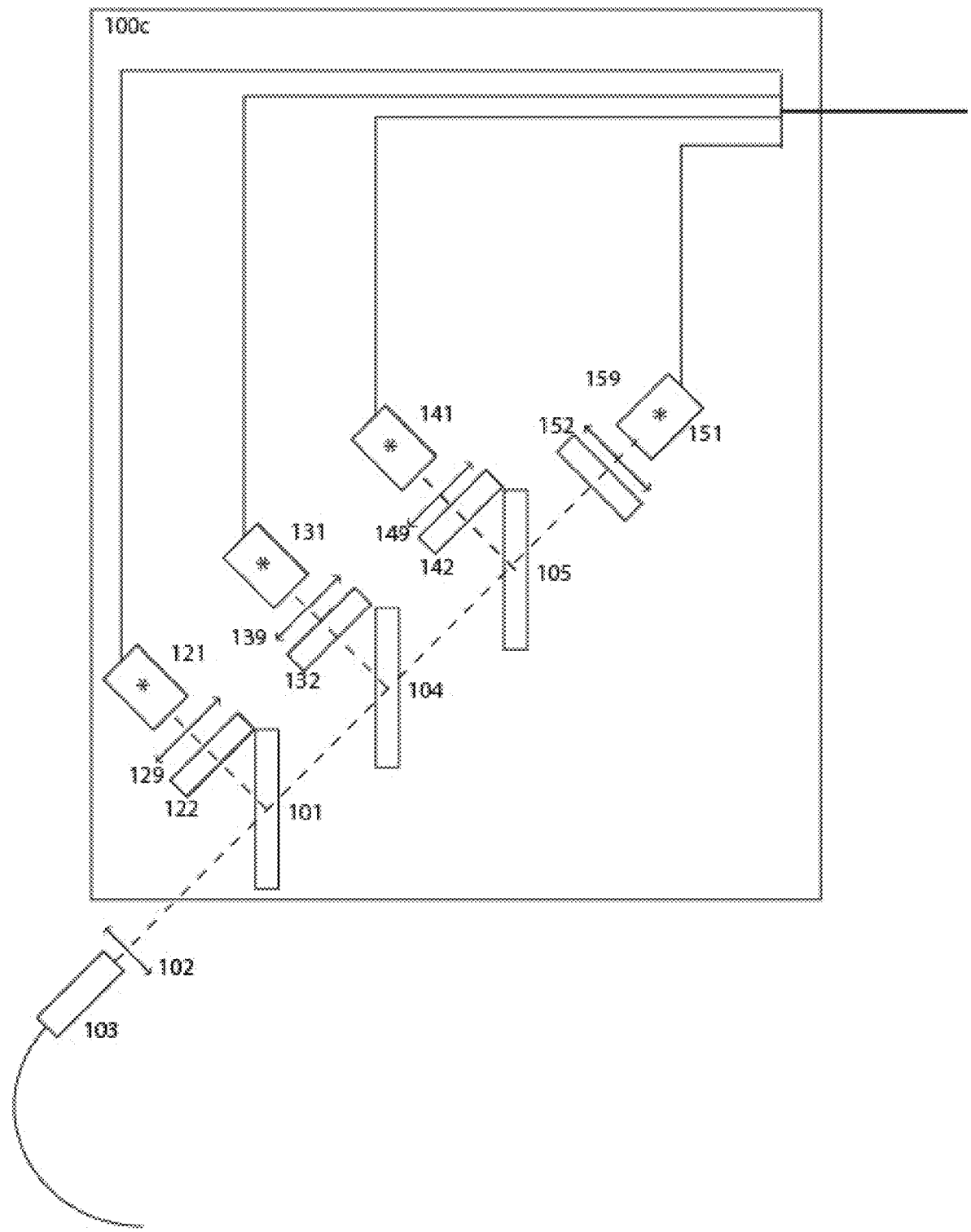
FIG. 13 shows a light source used in an embodiment of the invention.

In this alternative illumination system 100c the illumination lights are generated with several LED light sources as shown in FIG. 13. Instead of using two broadband LED sources this option uses multiple LEDs (121, 131, 141, 151 . . . ) that have a narrower spectral emission. This requires a more complicated lightning device, but on the other hand the output power can be increased dramatically and the intensity of the different LEDs can be balanced independently. Most monochrome LEDs still have a narrow emission with tails on the side spectrum. Thus excitation filters 122 132 142 152 may be optionally used in front of each LED to clean up the excitation spectra. Similar to the laser sources, the LED comprised of many narrowband sources are regarded as one illumination light and the LEDs can illuminate simultaneously, with full or partial time overlap, or may operate sequentially with no overlap. Nevertheless, any time combination within the exposure period associated with an illumination phase is considered as an accumulative light spectral distribution in one illumination phase.

Figure 14:
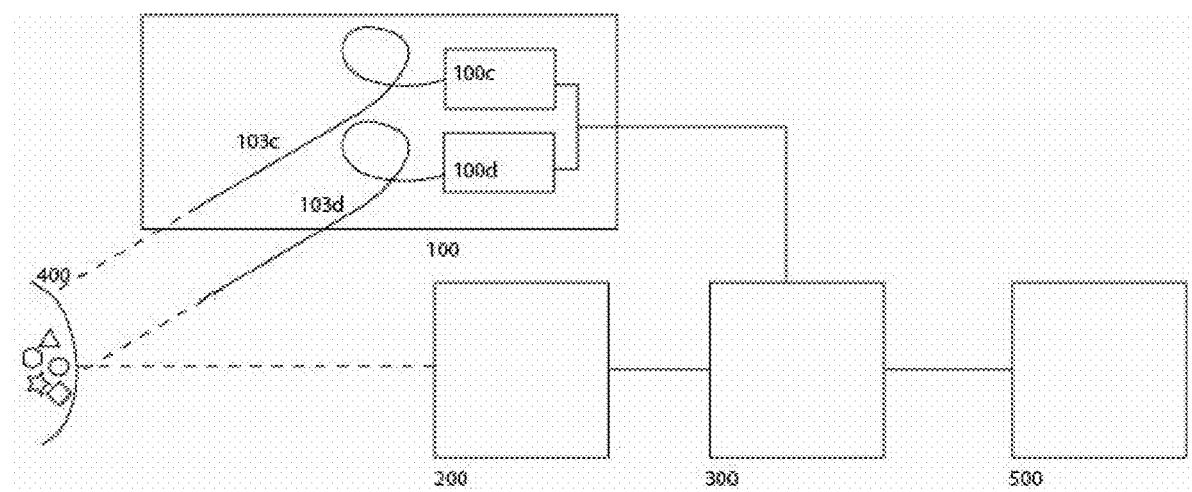
FIG. 14 shows a light source used in an embodiment of the invention.
Figure 15:
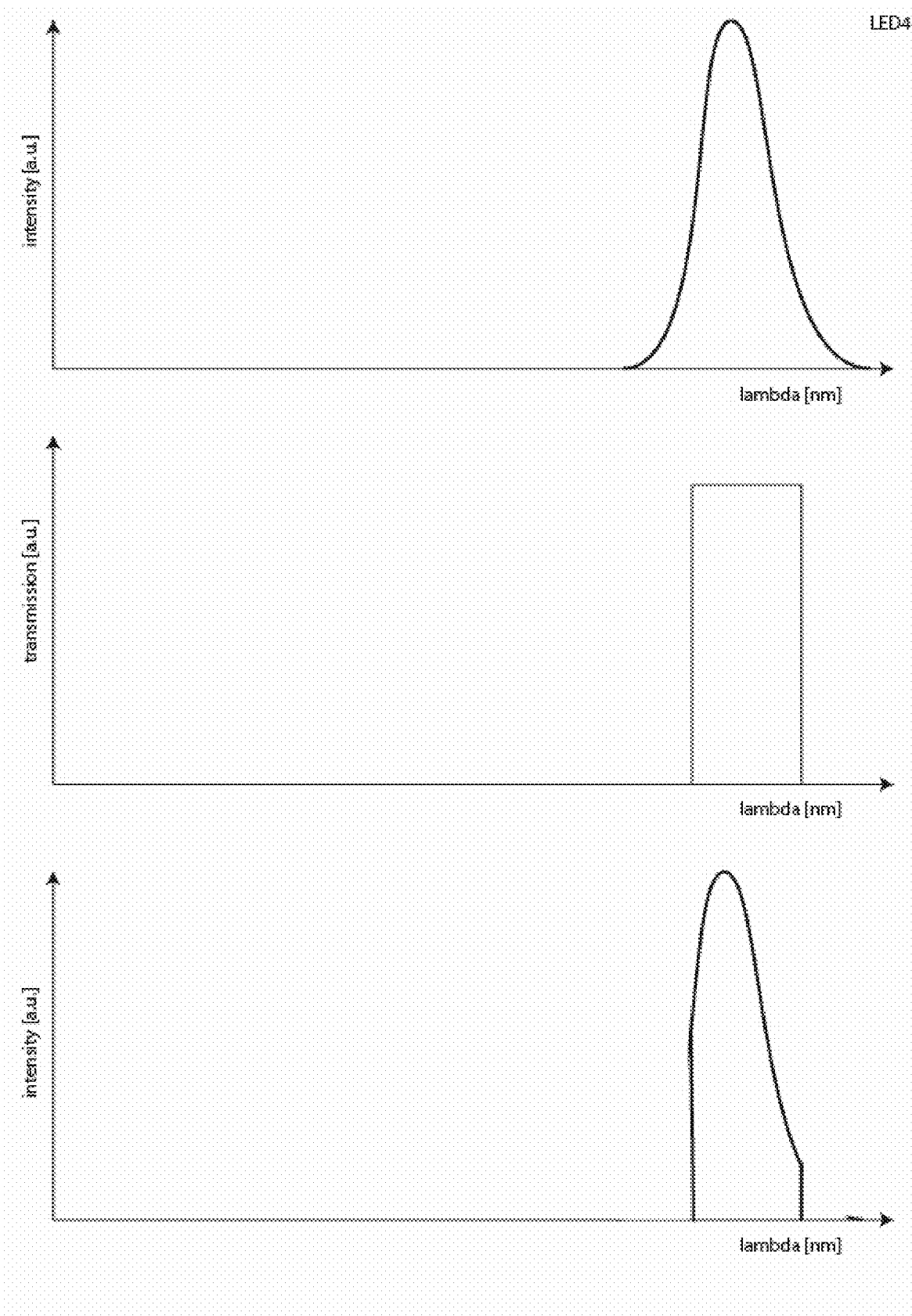
FIG. 15 shows an emission spectrum of a light source used in an embodiment of the invention, a transmission spectrum of a filter and the emission spectrum of the light source after filtering with the filter.
Figure 16:
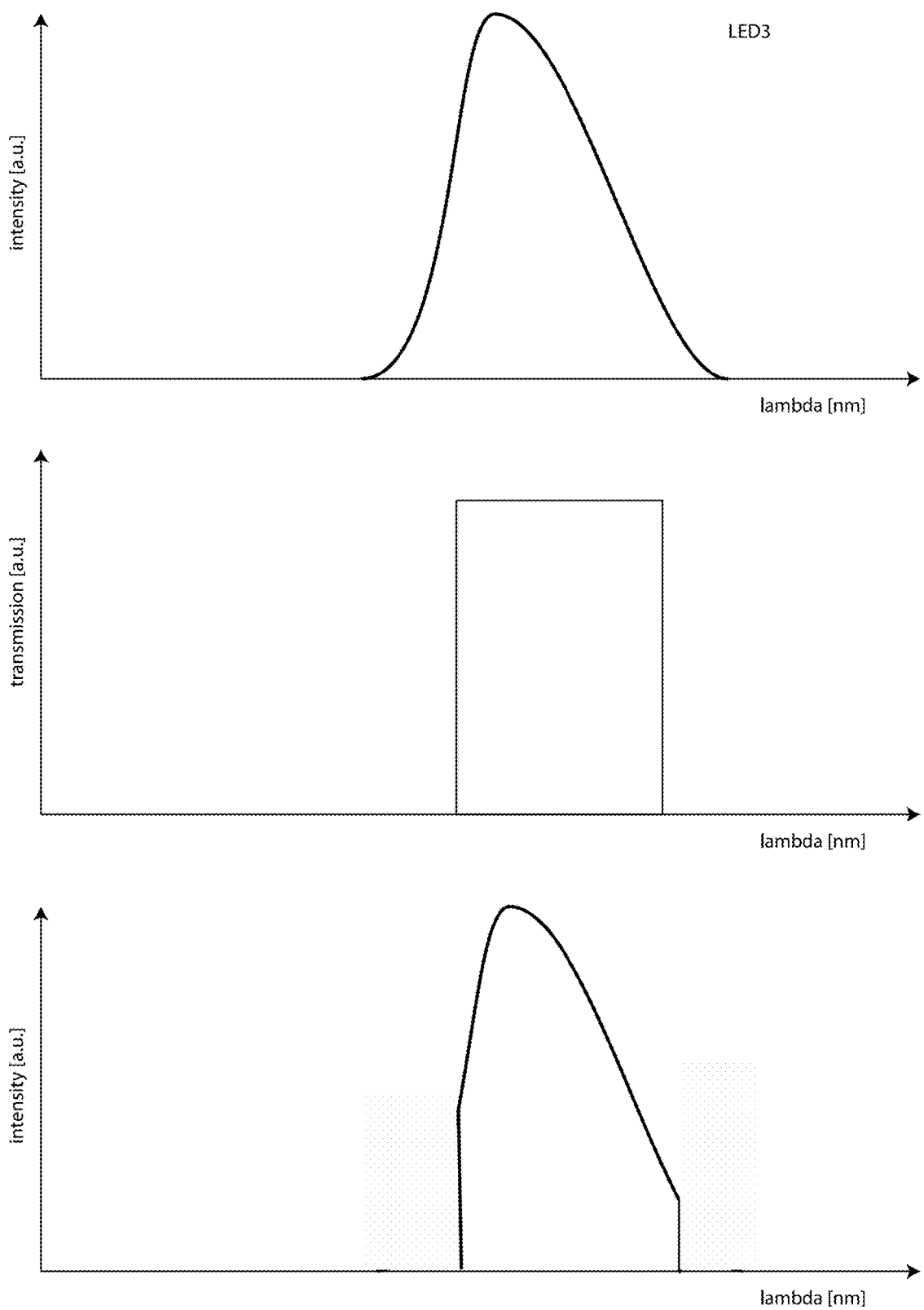
FIG. 16 shows an emission spectrum of a light source used in an embodiment of the invention, a transmission spectrum of a filter and the emission spectrum of the light source after filtering with the filter.
Figure 17:
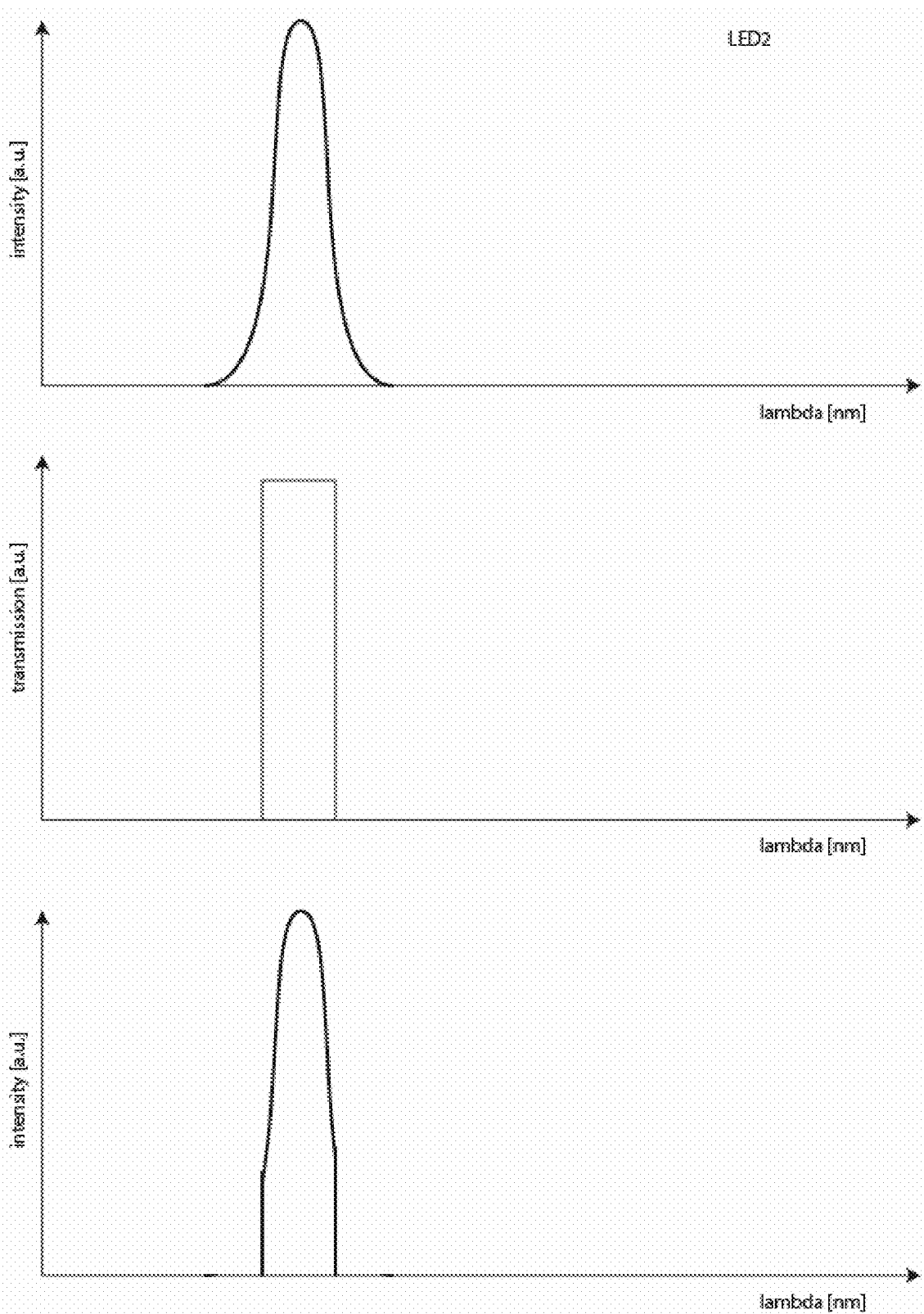
FIG. 17 shows an emission spectrum of a light source used in an embodiment of the invention, a transmission spectrum of a filter and the emission spectrum of the light source after filtering with the filter.
Figure 18:
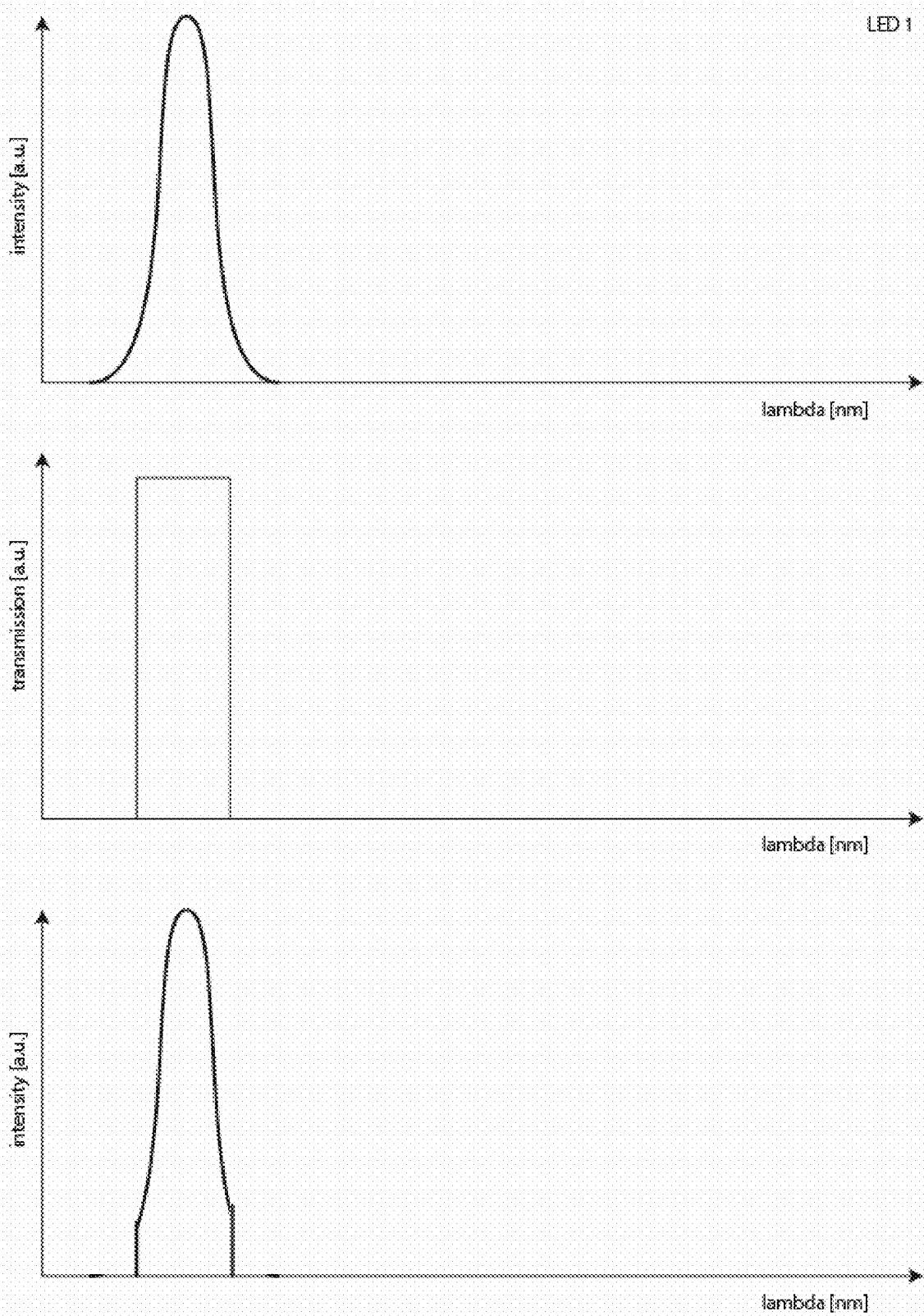
FIG. 18 shows an emission spectrum of a light source used in an embodiment of the invention, a transmission spectrum of a filter and the emission spectrum of the light source after filtering with the filter.

Such illumination sub-systems like the one described in FIG. 13 can be combined in a multiphase illumination system as shown in the schematic of FIG. 14. Therein, two light sources 100c and 100d are provided, each coupling its emitted light into fibers 103c and 103d, respectively for illumination of sample 400.

FIGS. 15 to 18 show each an emission spectrum of an LED light source, a transmission spectrum of a filter arranged in the emitted beam and an intensity spectrum of the emitted light after passing said filter. All four light sources together may replace one spectrally broadband light source.

Figure 19:
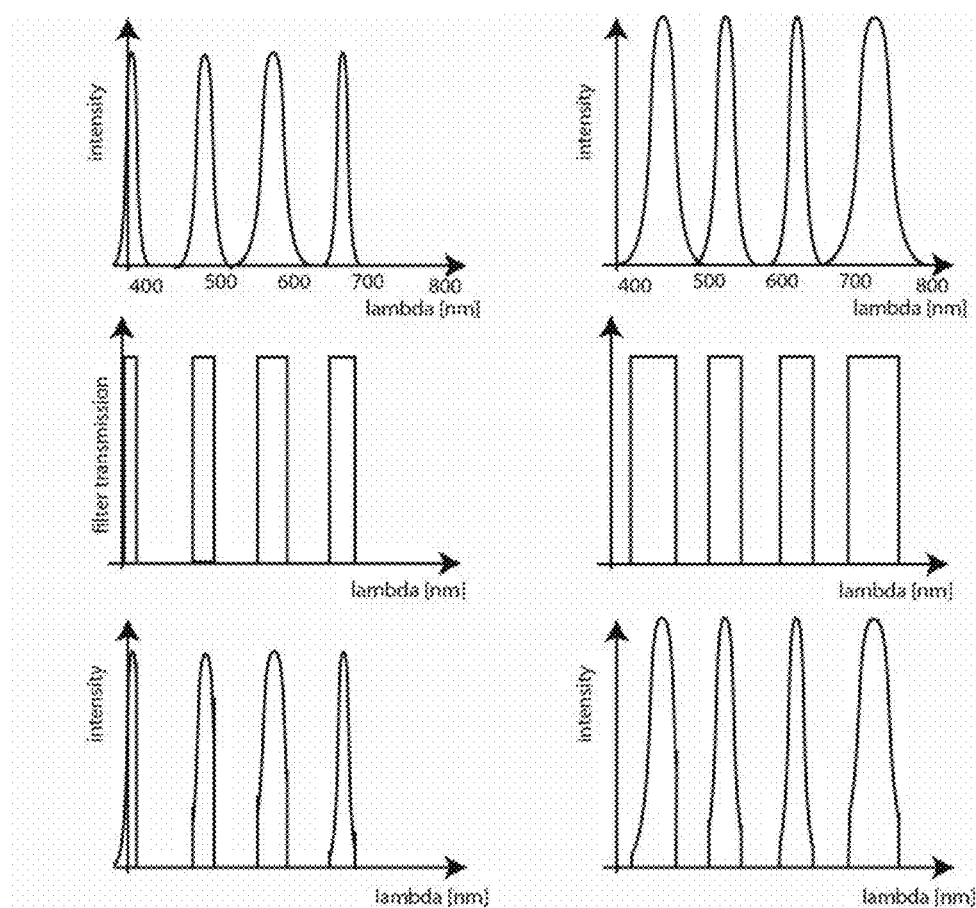
FIG. 19 shows an emission spectrum of a light source used in an embodiment of the invention, a transmission spectrum of a filter and the emission spectrum of the light source after filtering with the filter.
Figure 20:
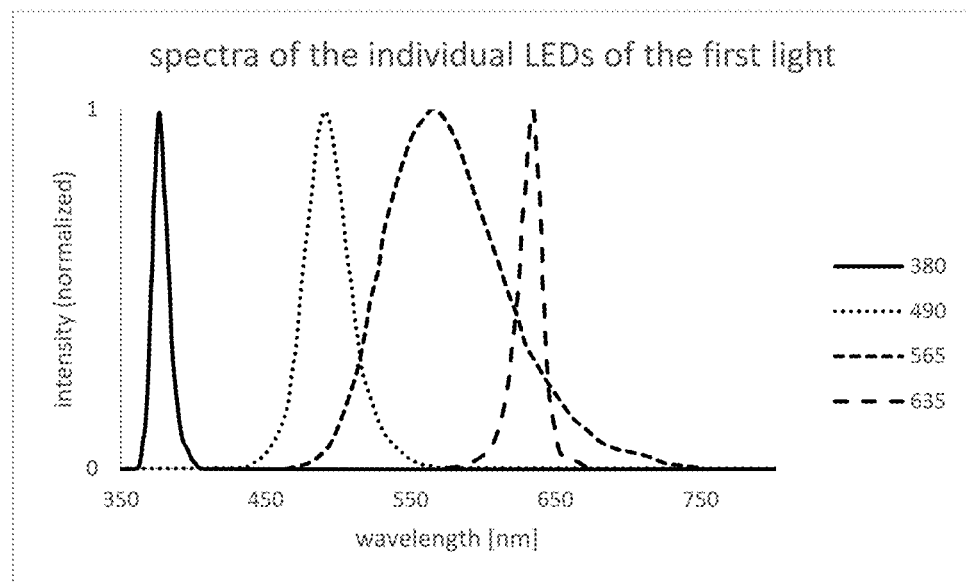
FIG. 20 shows emission spectra of various LEDs.

This preferred configuration has one excitation LED for each band of the multi-band filters. This would require 8 single different LEDs for quadruple band-pass filters. The spectra of such a configuration are shown in FIG. 19. FIG. 19 shows on the left side the spectrum of 4 LEDs, which constitute the first light source, the transmission spectrum of the corresponding filter and the resulting emission spectrum of the first light. On the right, corresponding spectra for the second light are shown. In the spectra, it is already implied, that each of the LEDs is associated with one light and thus with one phase. Though, the set of 4 individual LEDs can also be filtered using 4 individual single bandpass filters in front of each individual LED. Also the individual LEDs do not be strictly connected to one of the phases. FIG. 20 shows the real emission spectra of 4 commercially available LEDs with emission maxima at 380 nm, 490 nm, 565 nm, and 635.

Figure 21:
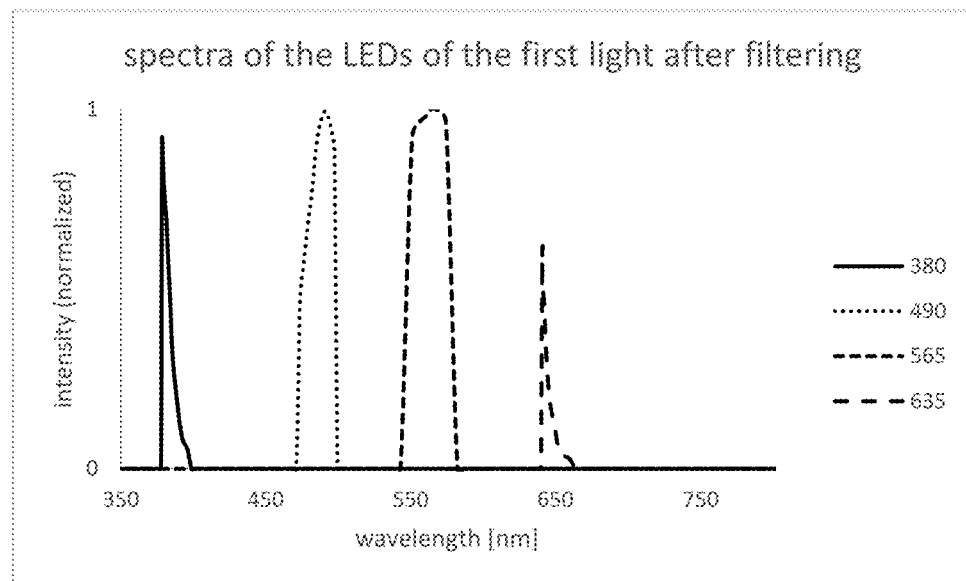
FIG. 21 shows the emission spectra of a light source after filtering with a filter.

FIG. 21, shows the resulting illumination spectral profile of the above four LEDs filtered by a quadruple band pass filter. The LED intensity is normalized for each of the 4 individual LEDs. In this case the first LED (380) marginally fits to the single band emission filter, the second and third LEDs (490 and 565) fit very well to their respective bandpass filter. The LED 4 (635) does not fit very well to the spectral transmission of its excitation bandpass filter.

[Using Shutters in the Lamp to Create the Illumination]

Figure 22:
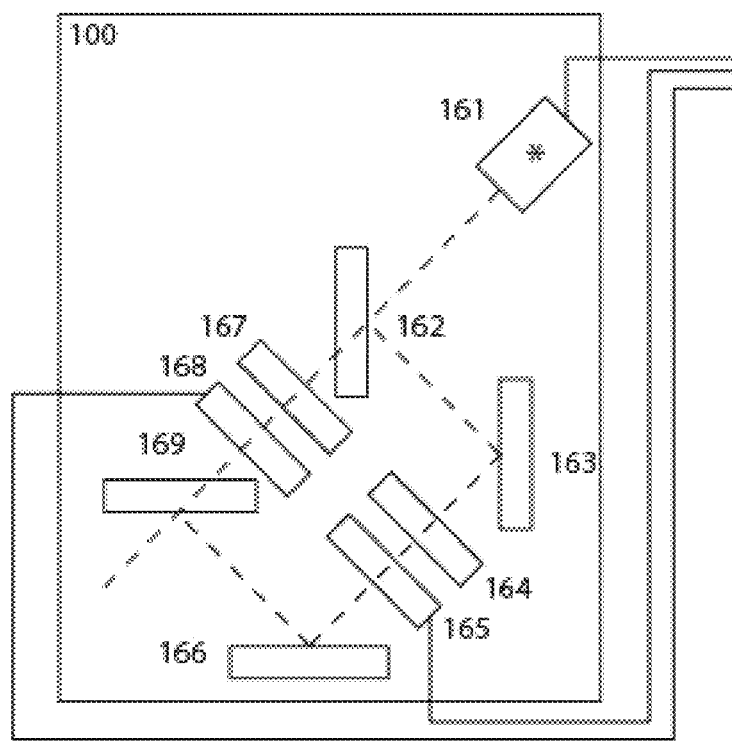
FIG. 22 shows a light source used in an embodiment of the invention.

In a further example shown in FIG. 22, temporal switching between different light sources is performed using optical elements 168 and 165 with variable transparency. In the simplest case these elements 168 and 165 with variable transparency are mechanical shutters. They can also be light modulators or acousto-optical devices. The broadband light emanating from a light source 161 is split by a polychroic mirror 162, then filtered by complementary excitation filters 164 and 167 and merged again by a polychroic element 169 similar to element 162. Mirrors 163 and 166 are used to align and guide the partial beam filtered by filter 165 in the system. For further improvement, the excitation light should be collimated to minimize losses and optimize filter performance in the system.

[Illuminating Through the Optical Detection System]

Figure 23:
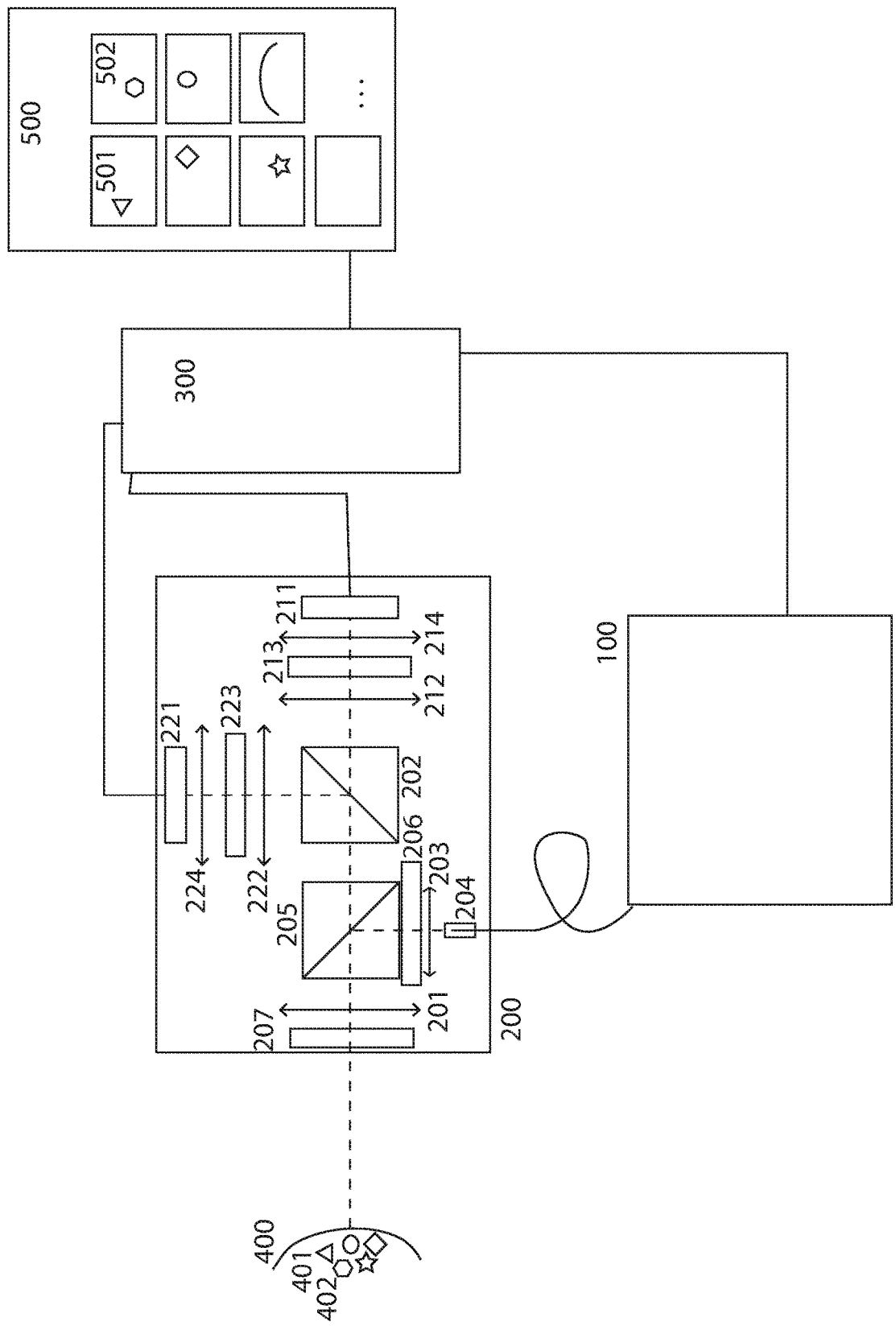
FIG. 23 shows an apparatus according to the invention.

In an alternative embodiment as shown in FIG. 23 the illumination system is configured to illuminate through the optical system. An optical light guide delivers the light from the multispectral illumination system 100 into a part of the imaging device 200 at a connector port 204. The illumination path may contain an optical lens system 203 to optimize the illumination on the object 400. The light is then filtered by a polarization filter 206 and subsequently combined with the imaging path with a beam-splitter device 205. Such a device can be a polarization beam splitter cube 205. The light is then passed through a rotatable half wave plate 207 which is rotating the angle of the polarization when light is passing through. This allows to reduce or eliminate reflections of reflected light depending on the position of the half wave plate. In an easy assembly the half wave plate 207 is located in front of the objective lens 201.

EXAMPLE 6

In the following various alternative detector systems are described as a basic embodiment. The descriptions contain mostly the differences between the different embodiments.

[Cube Beam Splitter]

Figure 24:
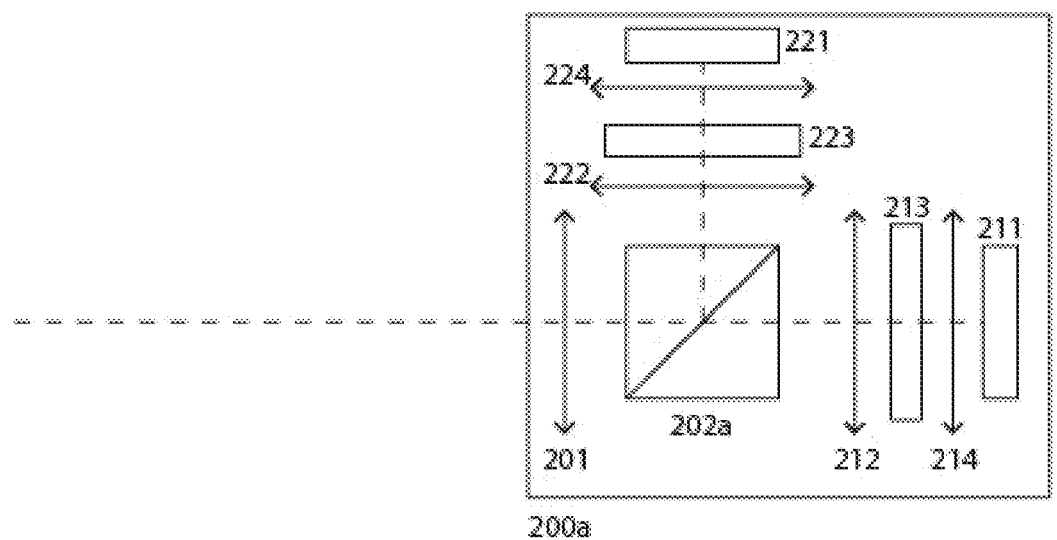
FIG. 24 shows a detection system used in an embodiment of the invention.

An alternative detection embodiment 200a is consisted of a cube beam splitter 202a instead of a mirror/dichroic mirror/polychroic mirror to split the beam into two separate beams as shown in FIG. 24. Cube beam splitters do not produce secondary images due to reflections on the non-coated side, and can in general have better optical flatness characteristics. The splitting element 202a has preferably a spectral transmission characteristic according to the emission filters 223 and 213. Alternatively the beam splitter can also be a neutral cube beam splitter (preferably a 50:50 beam splitter) or a polarization beam splitter.

[Multiple Cameras with Multiple Beam Splitters]

Figure 25:
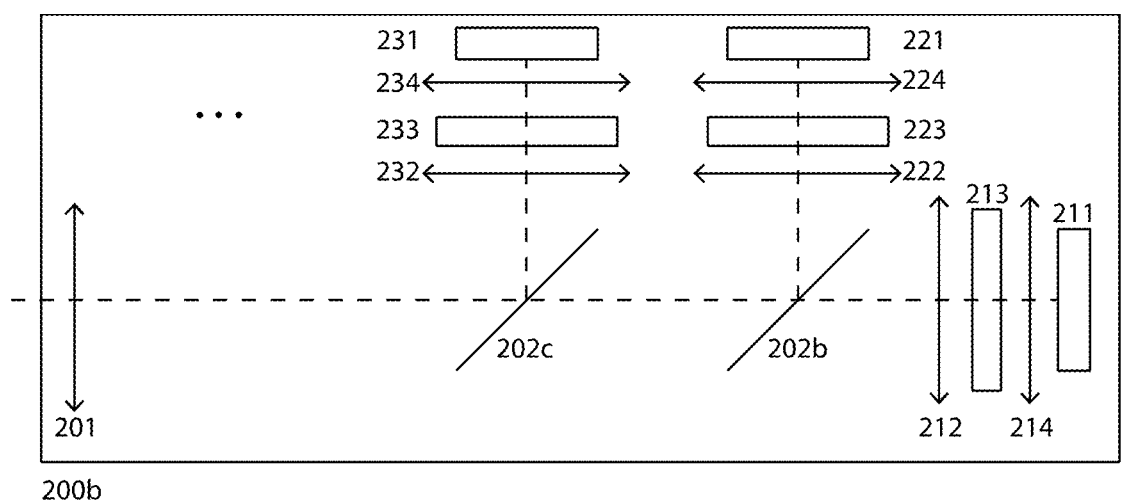
FIG. 25 shows a detection system used in an embodiment of the invention.

In an alternative embodiment as shown in FIG. 25 there are multiple sensor arrays (more than two, 211, 221, 231 . . . ), where more than one beam splitters (202b, 202c, . . . ) are used to divide the beam into different imaging paths. The filters 213, 223, 233 have complementary characteristics and are designed to support multiple detectors for multiphase operation of the system described later.

[Multiple Images on a Single Chip]

Figure 26:
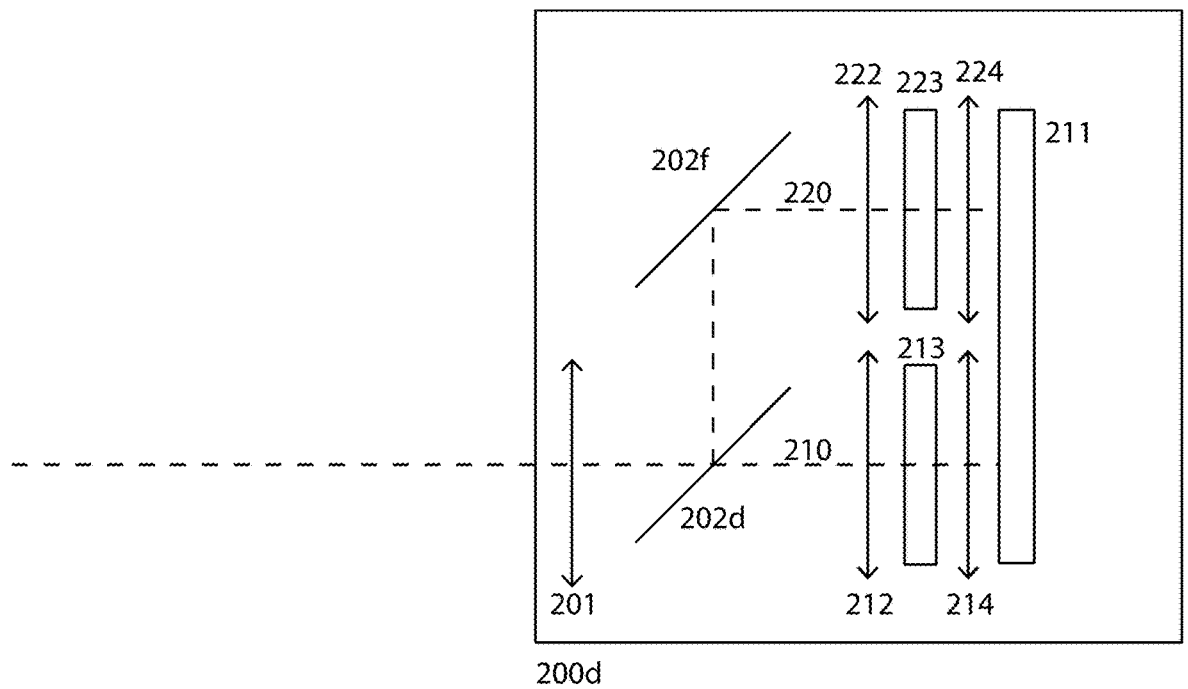
FIG. 26 shows a detection system used in an embodiment of the invention.

In an alternative configuration, the two sensors are replaced by one single sensor array with larger area (see FIG. 26). The optical path is preferably split by the dichroic mirror 202d and then a first image is formed on first half of the sensor 211 through the imaging path 210. The second image is aligned by the mirror 202f and then also imaged on the other half of the same sensor, but it is passing through an emission filter 223 complementary to the filter 213. In this way one sensor array detects two images.

Figure 27:
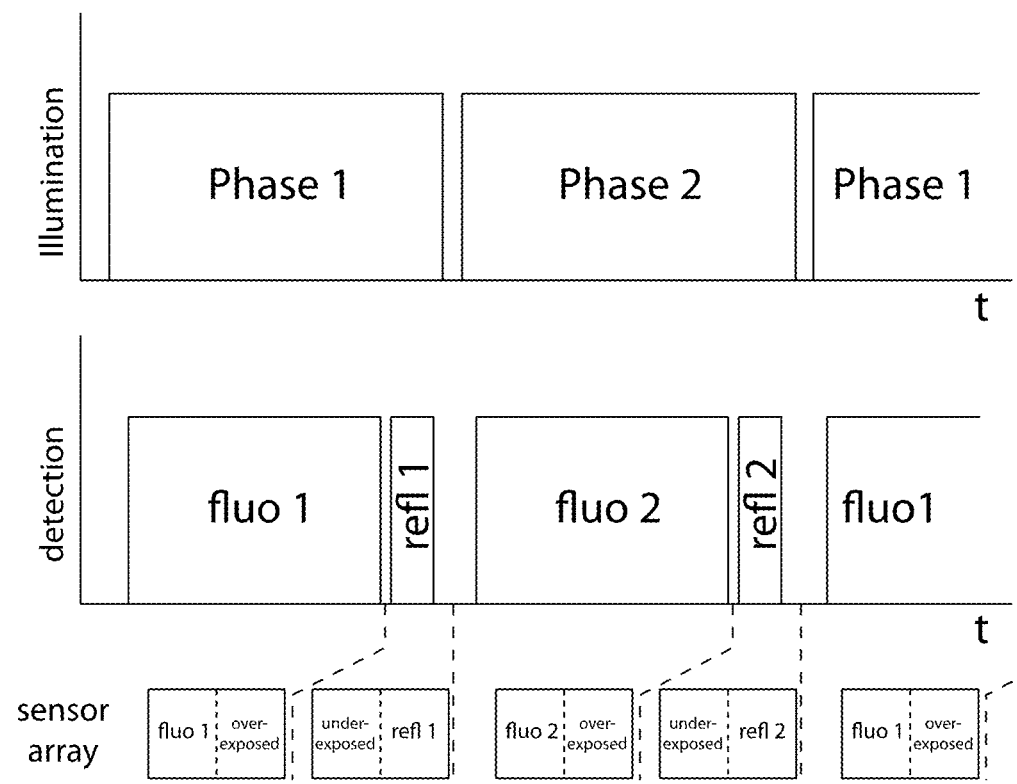
FIG. 27 shows the phase sequence of illumination and recording in an embodiment of the invention.

This setup is more compact and just requires one multi-channel sensor, but it exhibits additional challenges. Both, the fluorescence image and the reflectance image of each illumination phase need to be accommodated onto the same dynamic range of the sensor in order not to saturate or underexpose the sensor. If this is not possible with a single exposure, then a multiple exposure sequence may be used, for example as shown in FIG. 27. In this case, in order to expose correctly the image with the lower intensity (i.e. the fluorescence) a longer exposure time is necessary, and in this case the reflectance image is overexposed or saturated. During the same illumination phase a shorter exposure, the fluorescence image is under-exposed and the reflectance image is properly recorded within the dynamic range of the sensor. Similar timing sequence is used also in the other phase.

[Three Sensor Detector]

Figure 28:
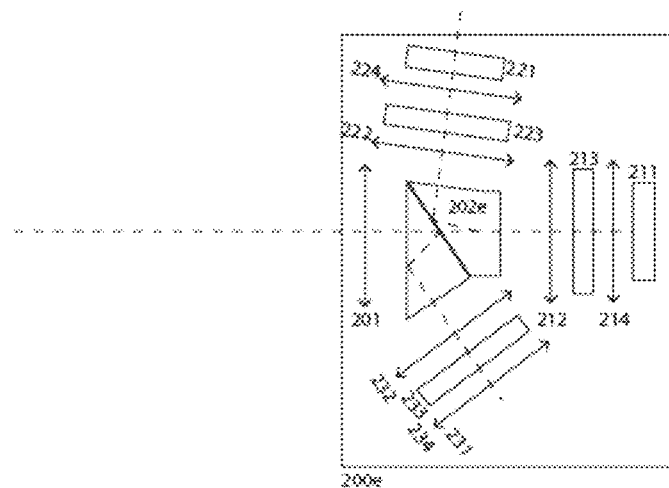
FIG. 28 shows a detection system used in an embodiment of the invention.

This setup uses a three-way beam splitting to split the beam to individual sensors (FIG. 28). This setup has preferably the same first lens element 201 as the setup 200a (FIG. 24). The beam splitting element 202e is different from 202a. It splits the beam into 3 different paths with a concept which is usually used for 3-CCD cameras. Instead of having 2 sensor paths, this setup uses 3 sensor paths 210, 220 and 230. Each path has its specific emission filter 213, 223 and 233 suitable for multiphase imaging to the sensors 211, 221 and 231. This approach can be extended to similar multiple beam splitters that offer multiple imaging paths (3 and more)

[Two Completely Separate Optical Systems]

Figure 29:
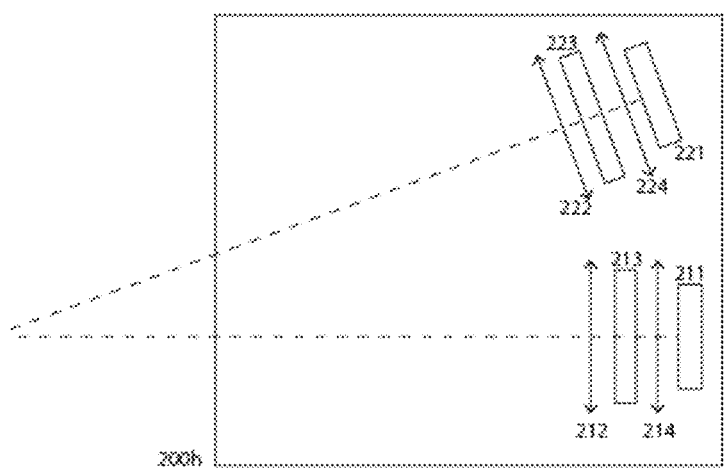
FIG. 29 shows a detection system used in an embodiment of the invention.

In an alternative detection embodiment (FIG. 29) detector 200h uses two completely separate optical detection paths and no beam splitting compared to 200a. Each path consist of an objective lens element 212 and 222, an emission filter 213 and 223, optionally an imaging adapter lens 214 and 224 and the sensors 211 and 221.

In contrast to the beam splitting approach, principally the images are not co-registered, i.e. there are small differences between them due to the different imaging perspective. Registration of the images is done at a later image processing step.

[Multi-channel Color Sensors]

The sensors described in the previous embodiments (211, 221 and so on) are in general multi-channel color sensors. This means that each individual sensor records the light field in multiple distinct spectral distributions. This can be achieved with various options: a) sensors that have microfilters in front of the pixels following the Bayer RGGB microfilter pattern or modifications of this like the RG(IR)B, the CMYG, b) any other filter mosaic patterns where each pixel records lighter with a distinct spectral distribution, and/or c) any further beam splitting, color filtering and imaging on monochrome sensors.

Figure 30:
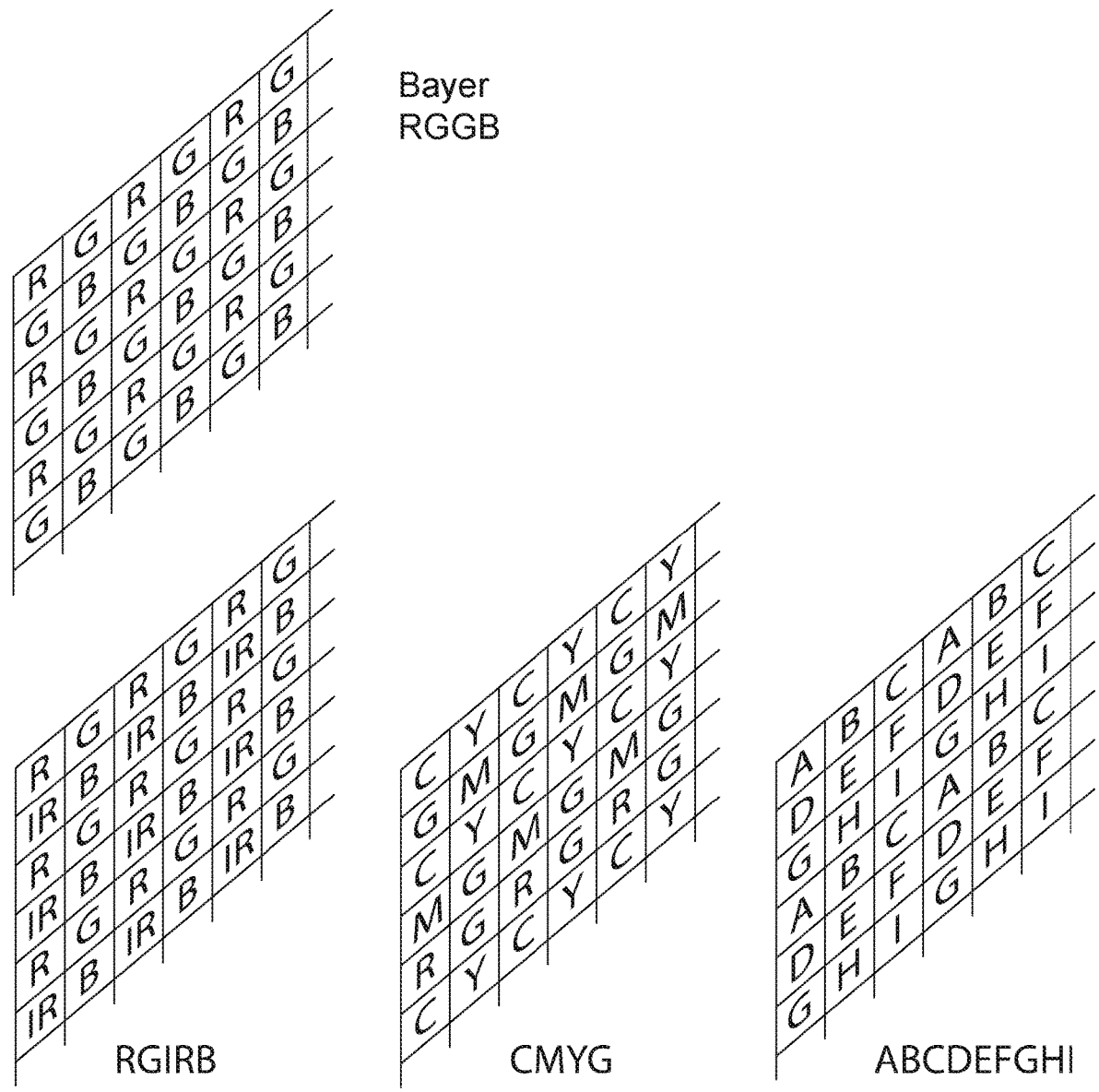
FIG. 30 shows the phase sequence of illumination and recording in an embodiment of the invention.

In general, the RGGB pattern achieves more accurate color reproduction, while the CMYG can be more sensitive (FIG. 30). The full resolution color image can be retrieved by demosaicing, which can take place in the camera hardware, or later in image processing. The microfilter pattern can in general be extended to multiple colors or spectral transmission profiles like ABCDEFGHI etc. An example like this is the lithographically patterned dichroic filter arrays as disclosed in U.S. Pat. No. 6,638,668 B2.

Figure 31:
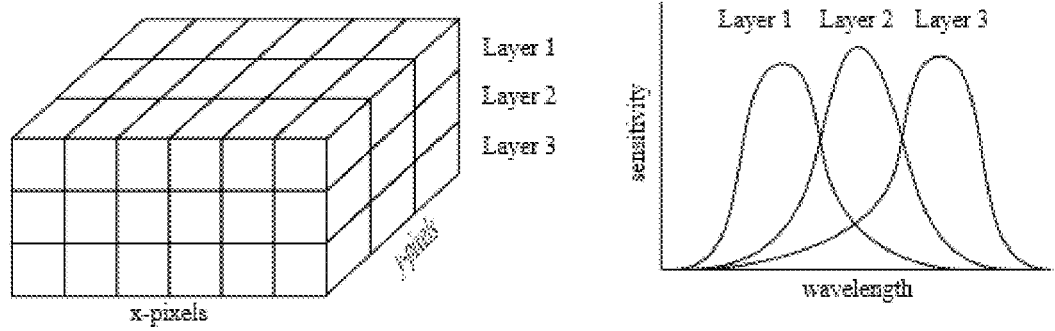
FIG. 31 shows the structure of a further multichannel color sensor used in an embodiment of the invention.

Alternatively, the multichannel color sensors can be based on Foveon X3 sensors [see U.S. Pat. No. 6,632,701] or similar technologies (FIG. 31). In contrast to the microfilter patterns, the Foveon sensor is having photosensors spatially arranged in x- and y direction and that multiple layers (layer 1, layer 2, . . . ) are vertically stacked. Each layer is sensitive to different spectral areas due to the silicon absorption and the different transmission depths for the layer above light, thus the images generated of each layer corresponds to different color. With this it is possible to achieve higher spatial resolution.

Figure 32:
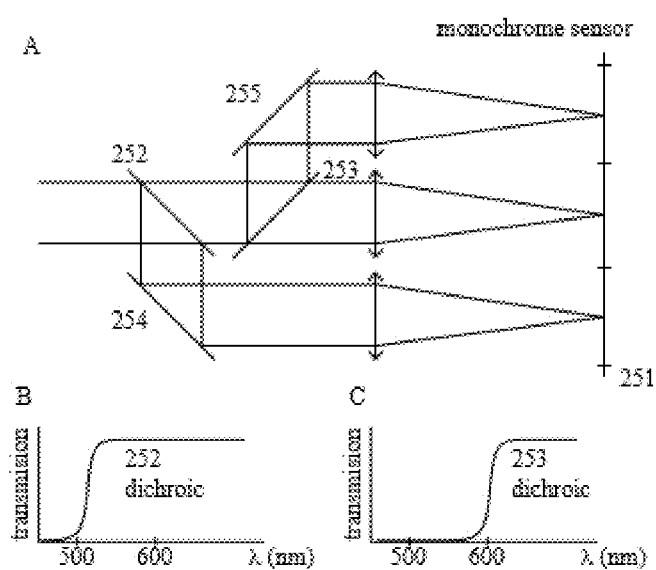
FIG. 32 shows the structure of a color sending system used in an embodiment of the invention.

In alternative embodiments, the multichannel sensors like 211 or 221 are replaced by a monochrome sensor 251 that the beam is split in three parts with the use of beam splitters/or mirrors 252 and 253 and filtered with filters or with dichroic mirrors (FIG. 32). Each filter or dichroic mirror has a particular transmission spectral profile, that separates the light to the different colors in FIGS. 32B and C. Different images are formed in the monochrome sensor each imaging a different spectral band.

Additionally, a multiple color channel can be implemented with multiple light splitting and filters, such as the prism 3-CCD geometry (as disclosed in U.S. Pat. No. 3,659,918). In this or similar light splitting implementations each path is filtered to carry light with the spectrum of the specific color, for example RGB. This approach can be extended to similar multiple beam splitters that offer multiple imaging paths (3 and more).

EXAMPLE 7

For most fluorescence applications ambient light needs to be avoided or blocked because its intensity is several orders of magnitude stronger than the intensity of the fluorescence light emerging from the fluorescent dye. Ambient light might come from the sun and pass through the windows onto the object or it might be emitted by the room lights. In current state-of-the-art systems usually, the environment is dark to avoid the intensive signal from ambient light in the fluorescence channels. As an alternative the specific wavelength regions of ambient light, which would pass the emission filter, may be blocked by filters. Unfortunately such filters are usually very expensive and it is not possible to cover big windows or room lights with such filters or they are just not available for any configuration.

The technology presented here describes an alternative idea allowing lighting in the room and to detect fluorescence. This invention has particular importance in surgical fluorescence imaging during open surgery. Two different options are presented. Both options operate with pulsed light sources as ambient illumination. In the first method/embodiment all the light in the imaging path is blocked during recording (referred in the claims as "holding the recording") of a frame, and the second method/embodiment uses the dead times of the sensor array in between frames for ambient illumination.

EXAMPLE 8

Figure 33:
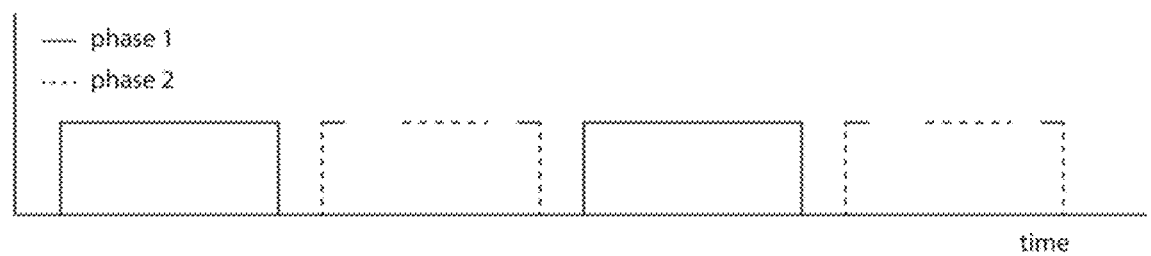
FIG. 33 shows the phase sequence of imaging in an embodiment of the invention.
Figure 33:
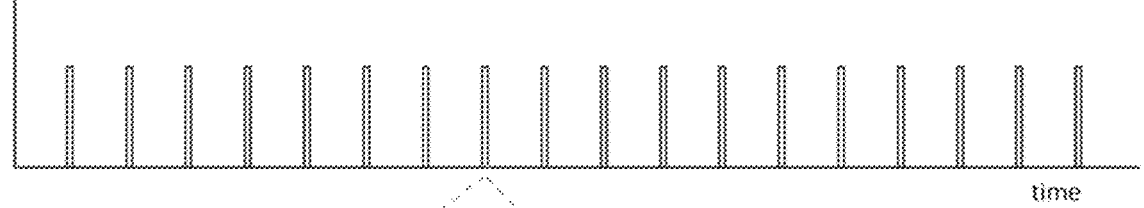
Figure 33:
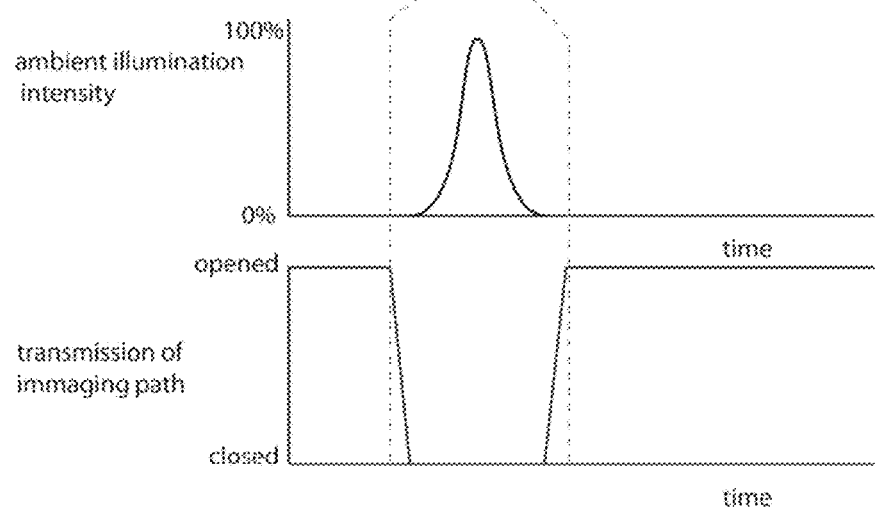

The illumination of the room lights are pulsed at a high frequency compared to maximum frequency perception of the human eye (for example at 200 Hz). The duration (duty cycle) of the pulses is typically a small fraction of the whole period (for example 5-20% of the period, typically 0.1-5 ms) as this allows longer exposure time for the fluorescence imaging (see FIG. 33). The light path for imaging fluorescence signals is blocked during the pulses of light of the ambient illumination. The figure shows the phases of the imaging system and the respective timing of the shutter device to allow ambient illumination.

DETAILED DESCRIPTION OF THE EMBODIMENT

Figure 34:
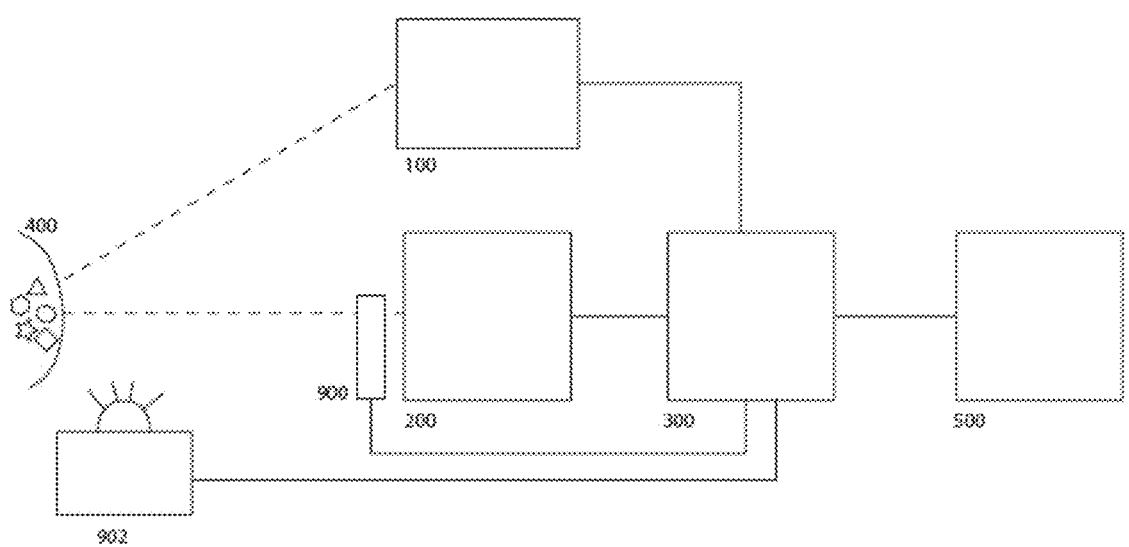
FIG. 34 shows an apparatus according to the invention.

In an embodiment shown in FIG. 34 a room illumination/ambient illumination light source 902 is provided, the light of which is coupled into the excitation light path. Further an additional shutter 900 is provided in the imaging path. In this embodiment the shutter is placed in front of the objective lens of the optical system 200 for simplicity reasons. Nevertheless it can also be placed at another position in the path. Alternatively, the shutter device 900 can be included in the imaging path directly in front of the sensor arrays. Both, the shutter 900 and the room illumination 902 are controlled from the control/processing unit 300.

When the shutter 900 is closed, it blocks all the light from entering the imaging/detection path and therefore light does not reach the sensor array system 200. The frequency of operation of the ambient illumination from source 902 is not necessarily connected to the frequency of operation of the fluorescence imaging system. It is preferable if the imaging system runs at 30-60 Hz to generate fluent stream of images of fluorescence and reflectance for the human eye. The ambient illumination 902 is preferably operated with a frequency which is higher so the human eye does not perceive any flickering in the room environment.

Preferably, the frequency of operation of the ambient lighting system 902 is a higher harmonic of the frequency of the imaging. In this case each sequentially taken picture is equally influenced by the closed imaging path. But it would also be possible to detect the ambient illumination timing and digitally correct for the influence of the slightly differently shuttered imaging path if necessary.

Figure 35:
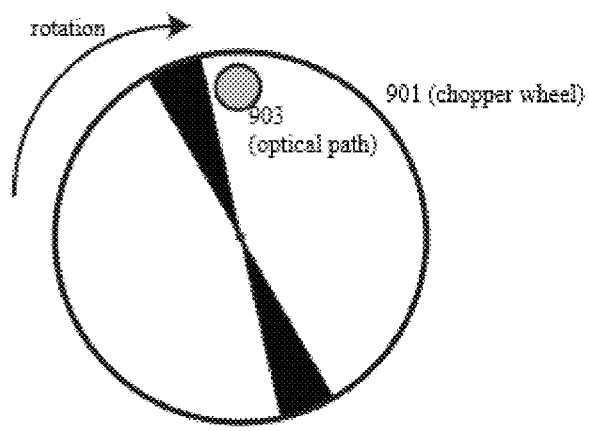
FIG. 35 shows a chopper wheel used in an embodiment of the invention.

The shutter 900 can be any electromechanical device that can allow or block light from propagation along the beam path. In a preferred embodiment the ambient light and the optical imaging path 903 is shuttered by a beam chopper wheel 901 (see FIG. 35) rotating at half the frequency of the shutter effect.

Chopper wheels 901 are a good choice to interrupt imaging paths with a certain frequency and usually operate at higher frequencies compared to optical shutters. Alternatively, a chopper wheel can be exchanged by different devices like electro optical modulator, SLMs, or acousto-optical modulators to hold the recording of the image by making the path opaque. In another alternative, the path is closed using polarization filters and using electronic devices with a variable polarization sensitive transmission of light. This also allows to effectively block the imaging path.

The light source can be any type of ambient light source that can operate with short pulses. The light source 902 preferably consists of electronically pulsed LEDs. Such LEDs are well suitable for the ambient illumination of an operation theater and can be pulsed at a very high frequency compared to the frequency of the human eye.

EXAMPLE 9

Figure 36:
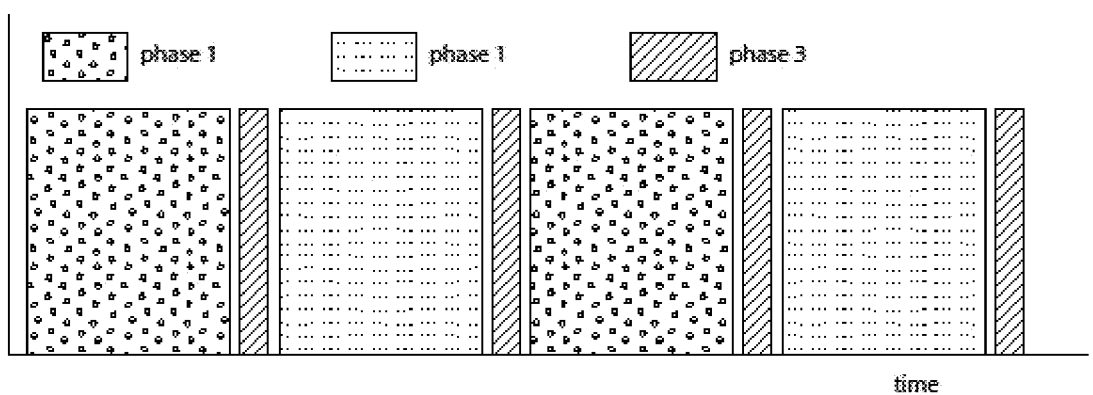
FIG. 36 shows the phase sequence of illumination in an embodiment of the invention.

An alternative embodiment as shown in FIG. 36 uses an additional phase (3rd phase) of illuminating light from a different light source always between the phases 1 and 2 of the imaging setup for ambient illumination. This phase runs at double the frequency of the other phases. The light source can either be independent similar to the light source 902 or be included in the light source 100 of the illumination system. The light emitted by this light source is not necessarily used for imaging, but may mainly be used to improve the visual perception for the human eye in the object and/or the surrounding environment.

In the basic embodiment the illumination of the imaging area is optimized only for the detection of image components and the image processing, and in particular for the unmixing of the different fluorophores. Typically, such an illumination is not optimal for the visual impression for a surgeon and may result a low image contrast and non-natural visual impression. The spectral distribution and intensity of the additional third illumination phase however is free to optimize the overall visual perception and brightness for the users (surgeon and medical personnel in the OR) as perceived accumulatively for all illumination phases.

The illumination pulses in the 3rd phase are short enough to fit in the dead time of the imaging sensors between the two phases (see FIG. 36) Usually the dead time occurs when transferring the data from the sensor 200 to the controlling unit 300. Thus short pulses with a high accuracy are required. If the imaging system works at a frequency of 30 Hz, the pulsed ambient illumination can work at double the frequency, i.e. 60 Hz. If we assume that the ambient illumination should just consume a duty cycle of 1%, the pulse width of the pulses should be in the order of 170 μs. If the ambient illumination consumes 5% duty cycle, the additional illumination phase provides a brighter field, and the pulsed ambient illumination duration is 800 μs.

EXAMPLE 10

In the preceding descriptions, the concept of a combined spectral and time multiplexing system is described using the scenario of two cameras and two different phases. Nevertheless, the same concept can be extended to further cameras and phases in more elaborate imaging scenarios. For example extent to 3 cameras and 3 phases, 4 cameras and 4 phases and so on. These allow for example to acquire additional spectral information on both the reflection and fluorescence images. Additionally, an alternative configuration operates in two phases, but may use more than two cameras, which offers an advantage in case two multichannel cameras cannot resolve essential features like fluorescence lifetime or sensitivity in the infrared region.

In this section, additional examples of higher dimension systems will be described in detail:

EXAMPLE 10A

Figure 37:
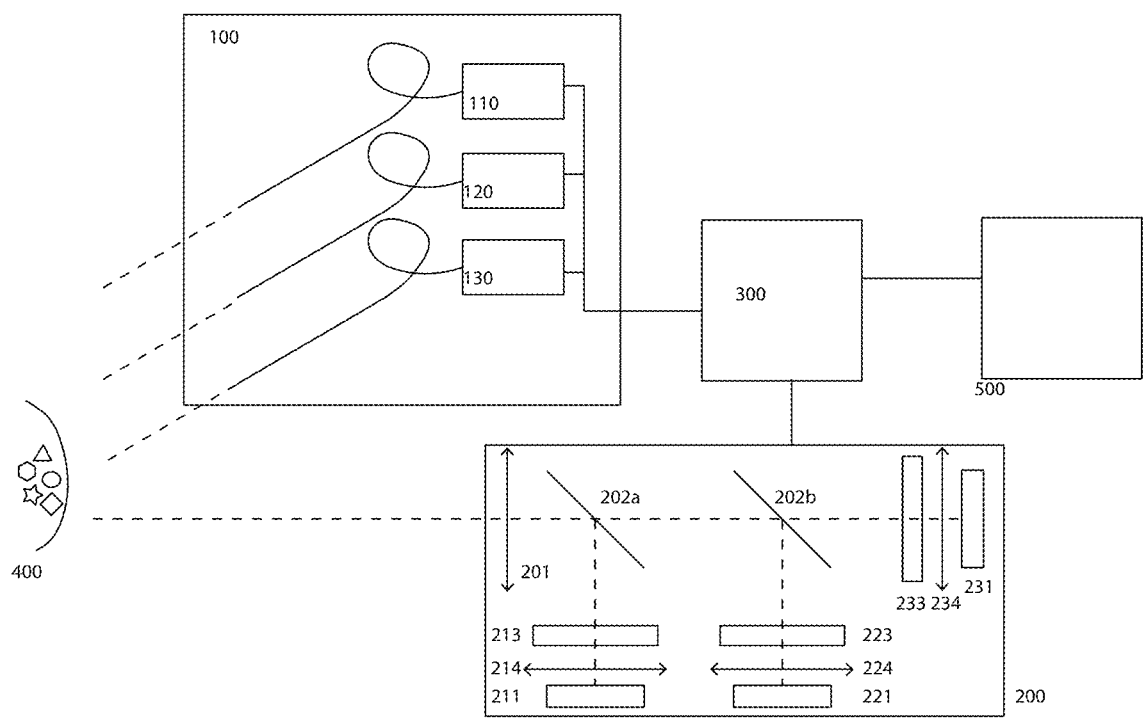
FIG. 37 shows an apparatus according to the invention.
Figure 38:
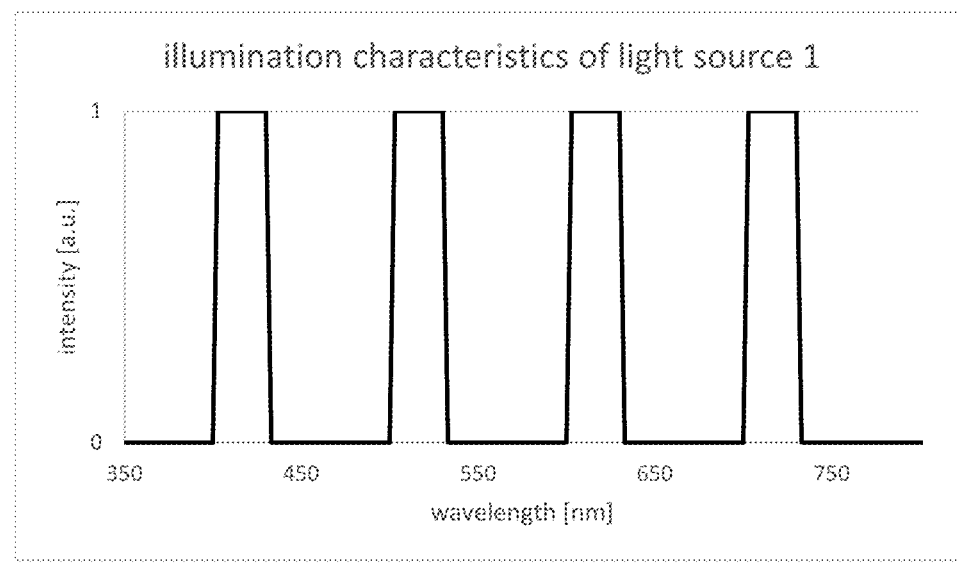
FIG. 38 shows the illumination characteristics of a light source used in an embodiment of the invention.
Figure 39:
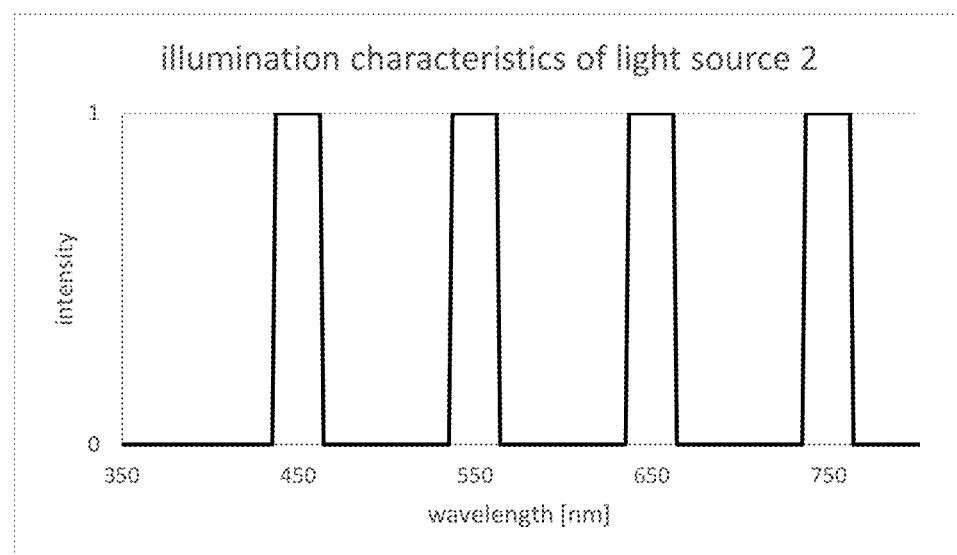
FIG. 39 shows the illumination characteristics of a further light source used in an embodiment of the invention.
Figure 40:
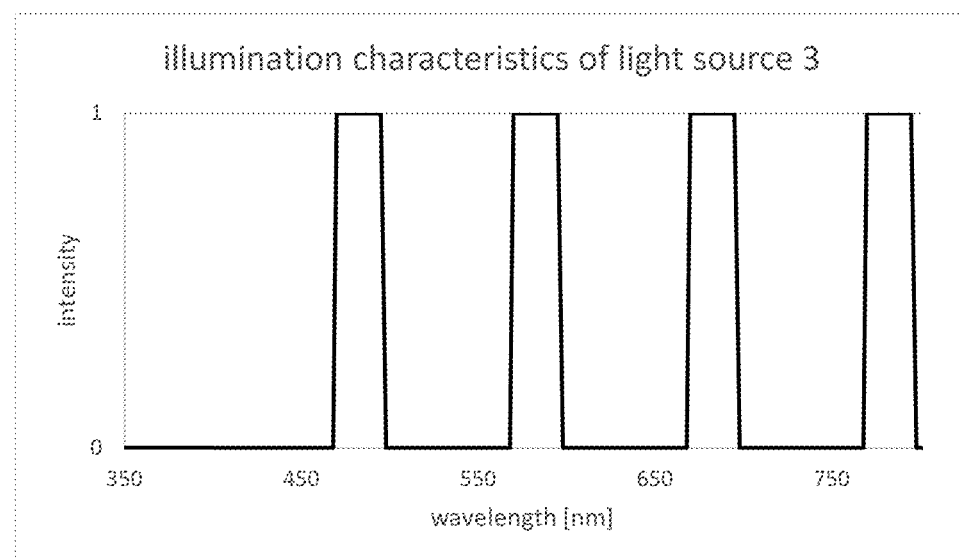
FIG. 40 shows the illumination characteristics of a further light source used in an embodiment of the invention.
Figure 41:
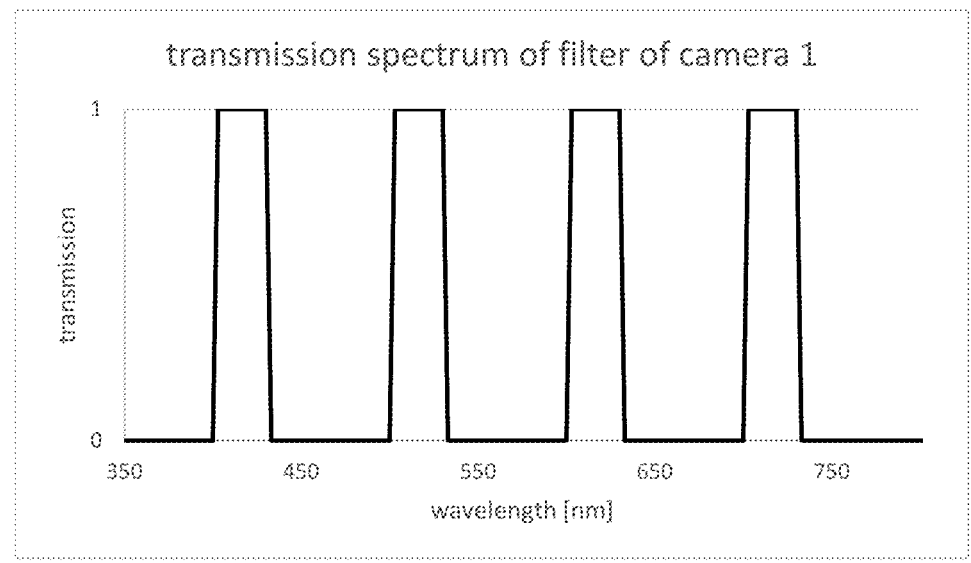
FIG. 41 shows the transmission characteristics of a filter used in an embodiment of the invention.
Figure 42:
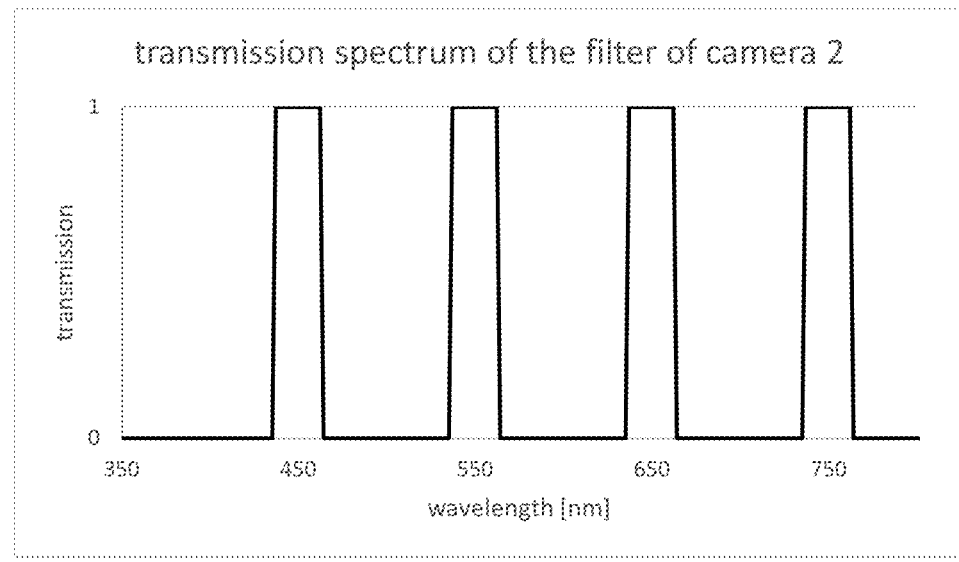
FIG. 42 shows the transmission characteristics of a further filter used in an embodiment of the invention.
Figure 43:
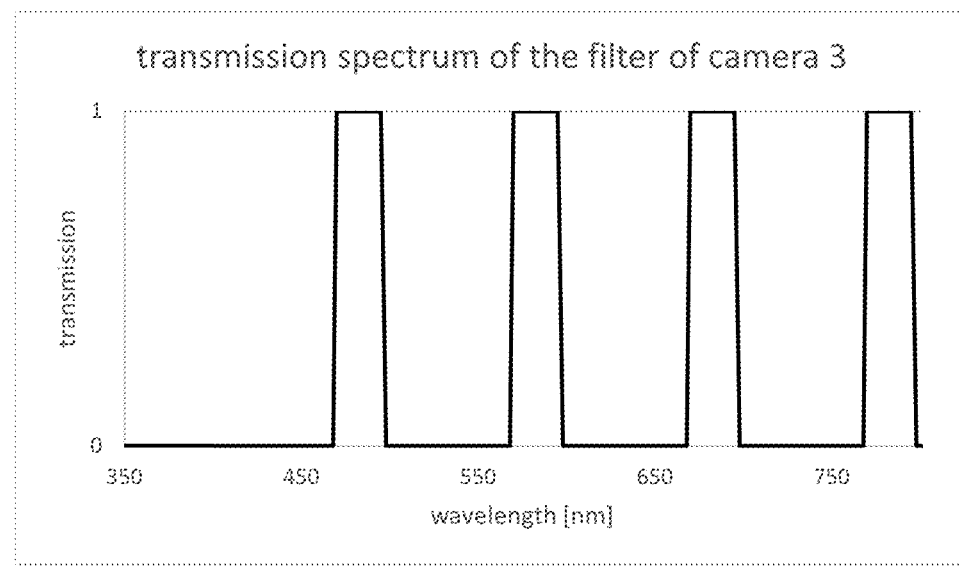
FIG. 43 shows the transmission characteristics of a further filter used in an embodiment of the invention.

Herein follows the description of a method and a system operating in 3 phases with 3 light sources and 3 cameras (see FIG. 37 showing schematics of the setup for 3 lights and three cameras). This example system has three different light sources 110, 120 and 130. The respective example emission spectra of the light sources are drawn in FIGS. 38, 39 and 40, respectively. The sample is illuminated in 3 phases by the light sources. In the first phase, the first light source illuminates the sample, in the second phase the second light source illuminates the sample and in the third phase the third light source illuminates the sample. The detector consists of 3 separate sensors 211 221 and 231 and the light is attenuated with the filters 213, 223, and 233 placed in front of each sensor respectively. Each sensor has a respective transmission filter that matches the emitted spectrum in of each respective light source placed in the imaging path, i.e. filter with the transmission characteristics shown in FIG. 41 is placed in front of sensor 1, filter shown in FIG. 42 in front of sensor 2, and filter shown in FIG. 43 in front of sensor 3. In this way there is a correspondence between the illumination spectra of each source to the light reaching each sensor. In each phase, all three sensors record a multichannel (color) image.

In table 1 the correspondence of illumination lights and filters to transmit or attenuate the reflected and emitted light is shown.

TABLE 1

Filter configuration for the different cameras

|  | Camera 1 | Camera 2 | Camera 3 |
|---|---|---|---|
| Light source 1 | Transmitted | Blocked | Blocked |
| Light source 2 | Blocked | Transmitted | Blocked |
| Light source 3 | Blocked | Blocked | Transmitted |

Figure 44:
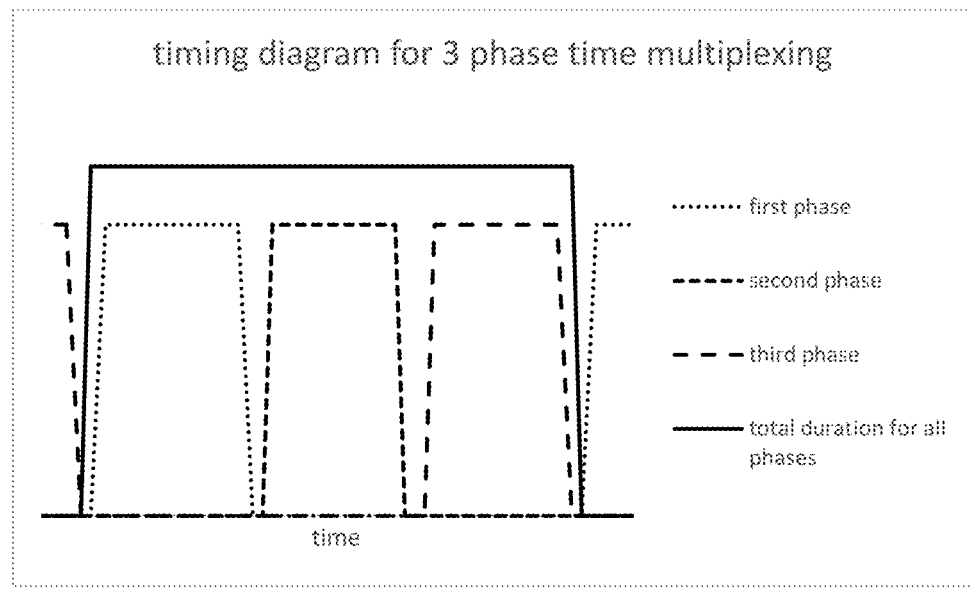
FIG. 44 shows the phase sequence of illumination in an embodiment of the invention.

In phase 1, sensor 1 records a reflection image in the spectral bands in which are illuminated by the light source 1. In this phase (phase 1), camera 2 and camera 3 cannot record the light emitted from the light source (source 1), as the filters placed in their imaging paths block the excitation light. But during this phase, each of these cameras records the fluorescence emission in the respective filter transmission bands. Similarly, in phase the second and third phase one camera detects the reflected excitation light and the other two the emitted fluorescence, as shown in the table 2. A full imaging cycle closes in 3 phases as shown in FIG. 44 and in total, the recording of all color channels of all cameras in each phase results in a combined data set (or a combined image) comprised of multiplexed spectral images, that each has different information, either of reflected excitation or fluorescence emission. The integration time of the each camera can vary in each phase to accommodate for the dynamic range of each image.

TABLE 2 camera function for each phase

|  | Reflection | Fluorescence |
|---|---|---|
| Phase 1 | Camera 1 | Camera 2, Camera 3 |
| Phase 2 | Camera 2 | Camera 1, Camera 3 |
| Phase 3 | Camera 3 | Camera 1, Camera 2 |

Assuming that each sensor has 3 detection channels (for example a standard RGB camera), after the completion of 3 phases, the system records combined reflectance images from 9 channels and combined fluorescence information from 18 channels.

If the number of detection channels $n_{CamChannels}$ of each camera is not three, the number of reflection channels $N_{refl}$ and the number of fluorescence channels $N_{fluo}$ of the entire system is $$N_{refl} = 3 \cdot 1 \cdot n_{CamChannels} \text{ and}$$

$$N_{fluo} = 3 \cdot (3-1) \cdot n_{CamChannels}$$

The major advantage of this setup is the increase in the total number of channels for fluorescence and reflection images, which enables the more accurate decomposition of the reflectance and fluorescence images to their accurate components after images processing. Compared to the two-camera setup, the filter design and manufacturing becomes more complicated, the image processing becomes more computationally intensive, and the total light reaching each sensor is less. The resulting lower light intensity and there for the lower S/N ratio can be compensated by longer exposure times, more sensitive camera sensors, and higher intensity light sources.

EXAMPLE 10B

Figure 45:
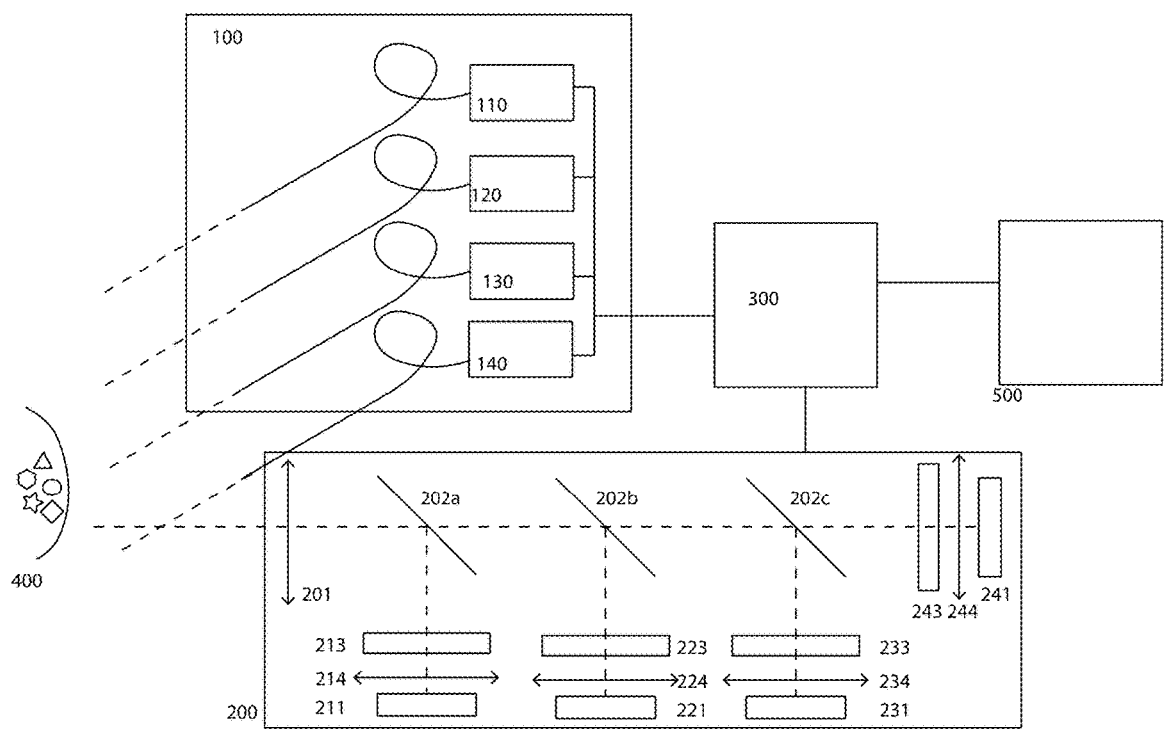
FIG. 45 shows an apparatus according to the invention.
Figure 46:
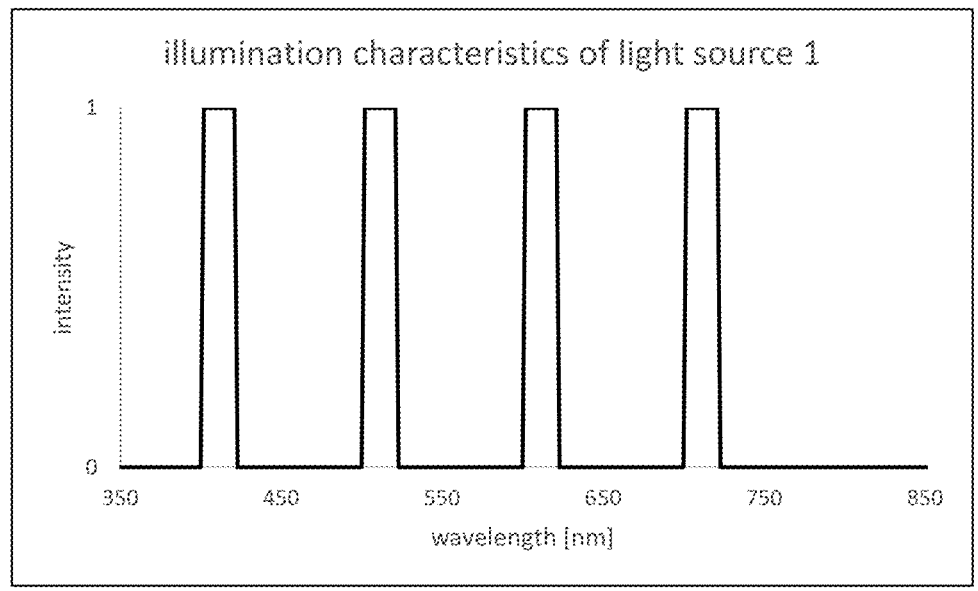
FIG. 46 the illumination characteristics of a light source used in an embodiment of the invention.
Figure 47:
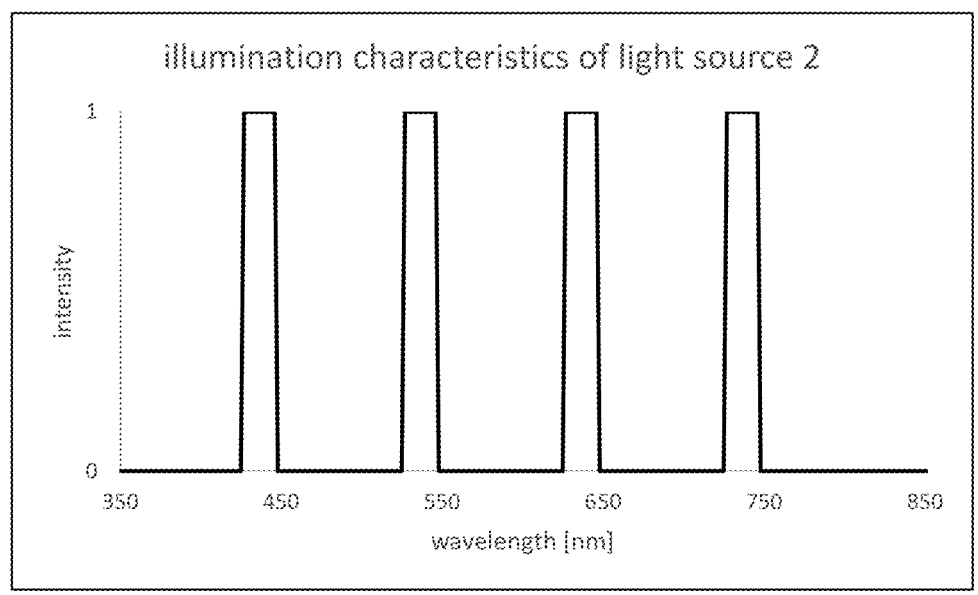
FIG. 47 shows the illumination characteristics of a further light source used in an embodiment of the invention.
Figure 48:
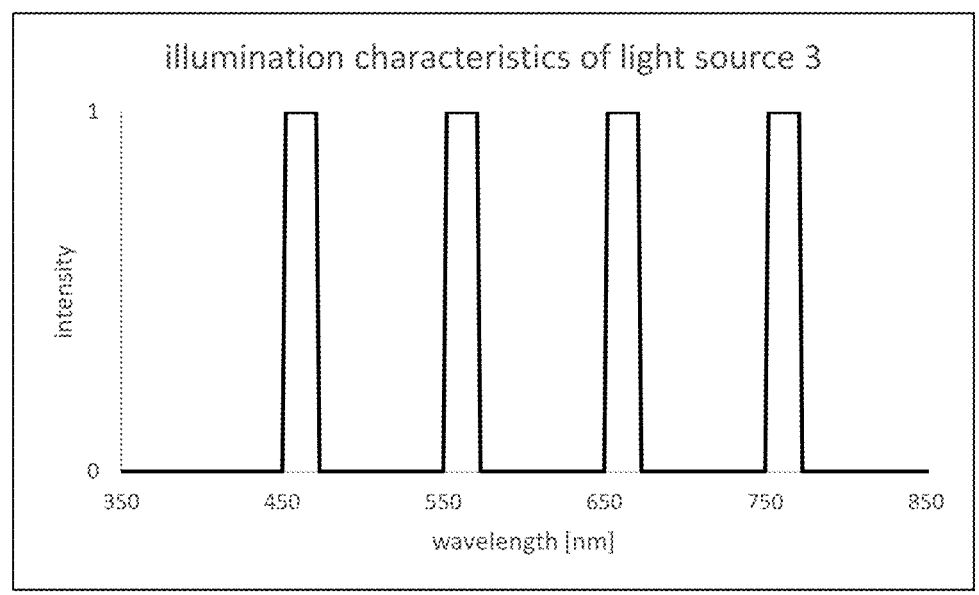
FIG. 48 shows the illumination characteristics of a further light source used in an embodiment of the invention.
Figure 49:
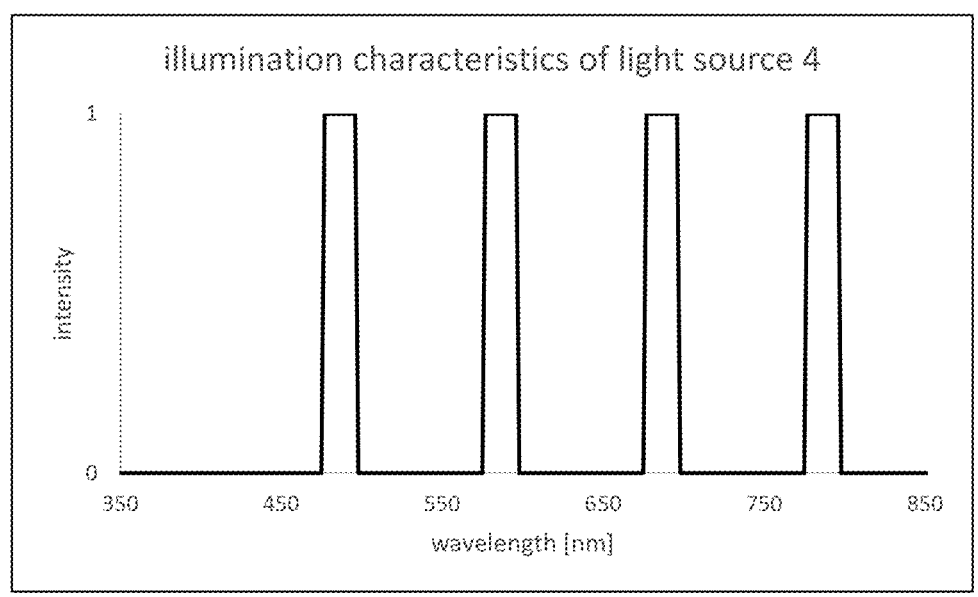
FIG. 49 shows the illumination characteristics of a further light source used in an embodiment of the invention.
Figure 50:
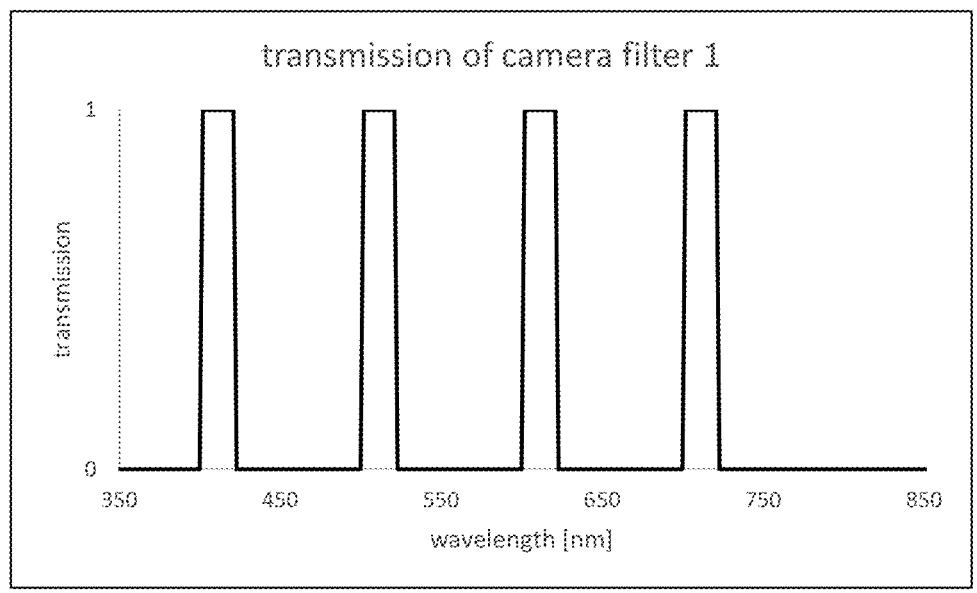
FIG. 50 shows the transmission characteristics of a filter used in an embodiment of the invention.
Figure 51:
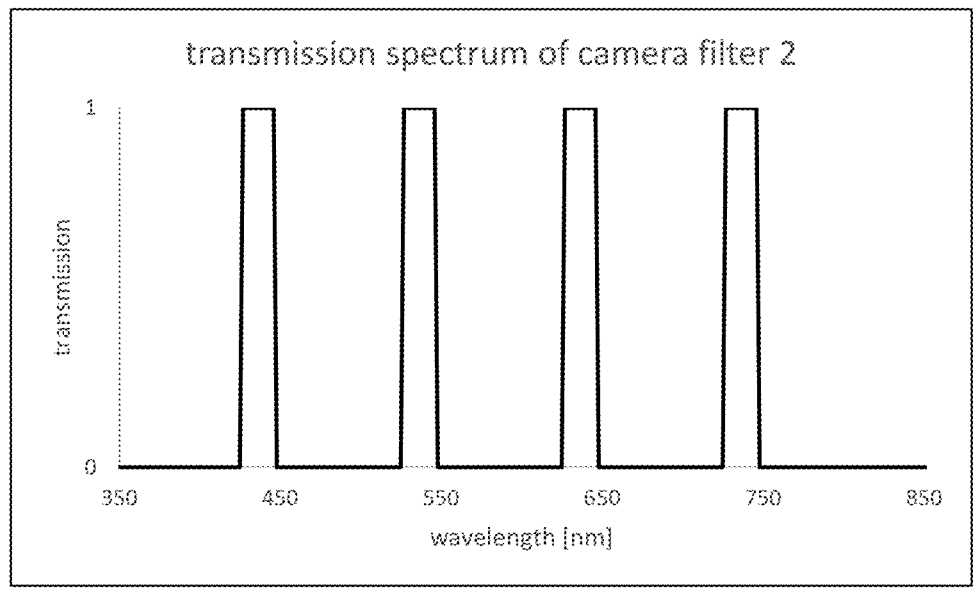
FIG. 51 shows the transmission characteristics of a further filter used in an embodiment of the invention.
Figure 52:
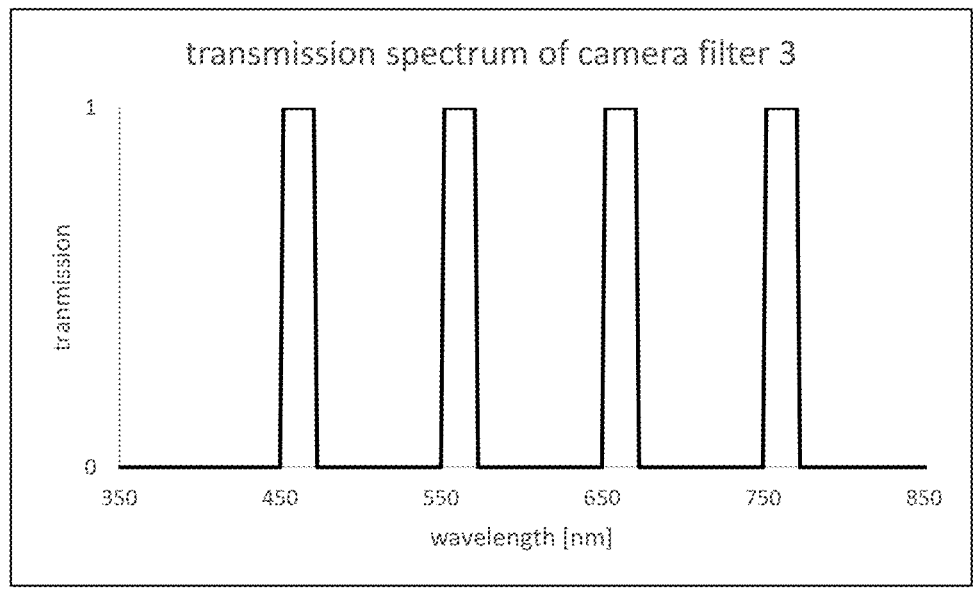
FIG. 52 shows the transmission characteristics of a further filter used in an embodiment of the invention.
Figure 53:
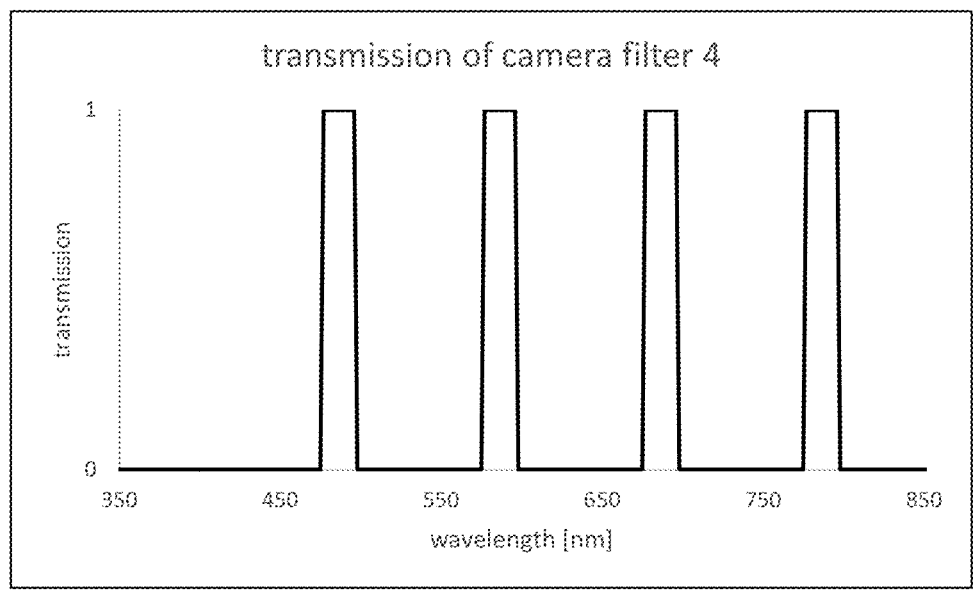
FIG. 53 shows the transmission characteristics of a further filter used in an embodiment of the invention.

The principle of time and spectral multiplexing can also be extended to 4 phases, 4 light sources and 4 cameras as shown in FIG. 45. The sample is illuminated with light source 110 in phase 1, with light source 120 in phase 2, with light source 130 in phase 3 and with light source 140 in phase 4. The 4 different illumination spectra of the light sources are illustrated in FIGS. 46, 47, 48 and 49. The characteristics of the different filters 213, 223, 233, and 243 in front of the cameras which are specified in table 3 with respect to the spectral characteristics of the light sources, and the spectral transmission profiles of the filters are shown in the FIGS. 50, 51, 52, 53, respectively. In this case transmitted means that is a rather large part of the intensity is actually transmitted while blocked means that the light intensity is attenuated by the filter preferably by a factor of $10^{\wedge}-4$ to $10^{\wedge}-6$.

TABLE 3

Filter design for the different cameras with respect to the illumination spectrum of the different light sources

| Filter in front of | Camera 1 | Camera 2 | Camera 3 | Camera 4 |
|---|---|---|---|---|
| Illumination Spectrum of Light source 1 | Transmitted | Blocked | Blocked | Blocked |

TABLE 3-continued

Filter design for the different cameras with respect to
the illumination spectrum of the different light sources

| Filter in front of | Camera 1 | Camera 2 | Camera 3 | Camera 4 |
|---|---|---|---|---|
| Illumination Spectrum of Light source 2 | Blocked | Transmitted | Blocked | Blocked |
| Illumination Spectrum of Light source 3 | Blocked | Blocked | Transmitted | Blocked |
| Illumination Spectrum of Light source 4 | Blocked | Blocked | Blocked | Transmitted |

The sample is imaged splitting the imaging path into 4 partial paths and in each path the light is filtered and then focused onto the respective cameras. The filters in front of each camera transmit the light, which is emitted by the light source of the same number, but blocks all the light emitted from the other 3 light sources. Each camera records in one phase a reflection image and in the 3 other phases a fluorescence image. The table 4 shows the recording combinations.

TABLE 4

Recording of fluorescence and reflection images
for the different cameras in different phases

|  | Reflection | Fluorescence |
|---|---|---|
| Phase 1 | Camera 1 | Camera 2, Camera 3, Camera 4 |
| Phase 2 | Camera 2 | Camera 1, Camera 3, Camera 4 |
| Phase 3 | Camera 3 | Camera 1, Camera 2, Camera 4 |
| Phase 4 | Camera 4 | Camera 2, Camera 3, Camera 3 |

Figure 54:
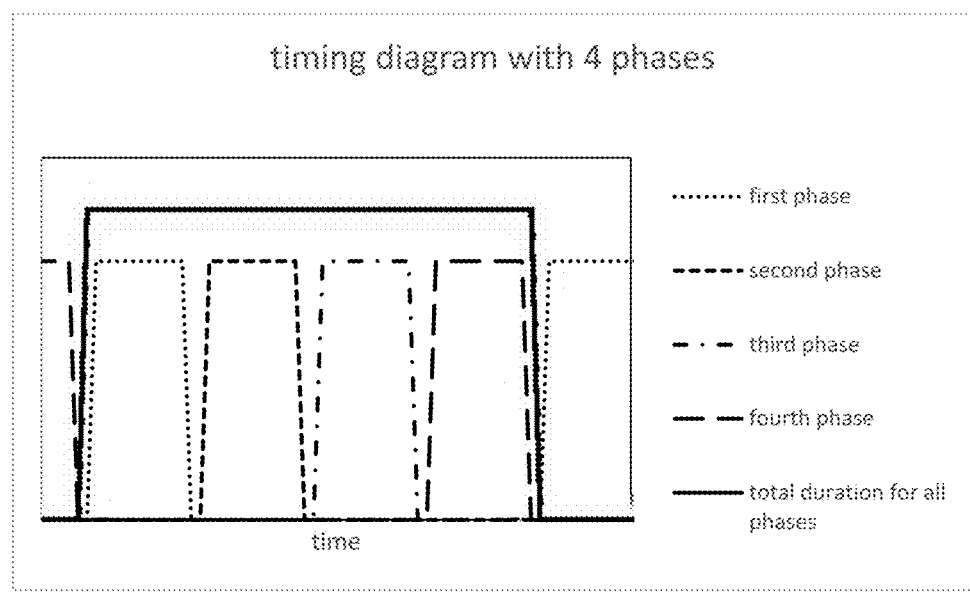
FIG. 54 shows the phase sequence of illumination in an embodiment of the invention.
Figure 55:
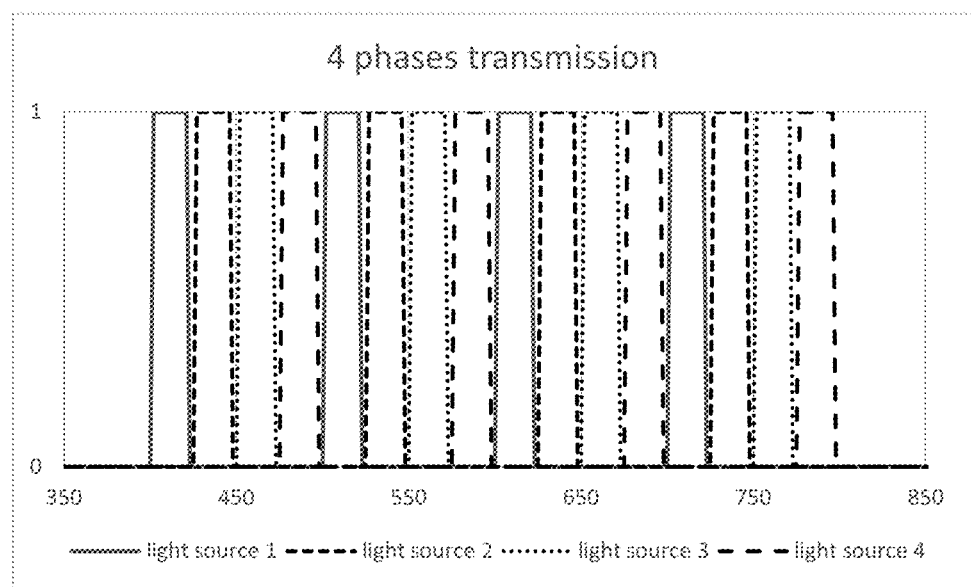
FIG. 55 shows the transmission characteristics of the filter in an embodiment of the invention.

If the number of detection channels $n_{CamChannels}$ of each camera is not three, the number of reflection channels $N_{refl}$ and the number of fluorescence channels $N_{fluo}$ of the entire system is $N_{refl} = 4 \cdot 1 \cdot n_{CamChannels}$ and $N_{fluo} = 4 \cdot (4-1) \cdot n_{CamChannels}$ As shown in FIG. 54, a full imaging cycle closes in 4 phases and in total, the recording of all color channels of all cameras in each phase results in a combined data set (or a combined image) comprised of multiplexed spectral images, that has different information, either of reflected excitation or fluorescence emission. The integration time of the each camera can vary in each phase to accommodate for the dynamic range of each image. A combined plot with all the transmission spectra for the four phases is shown in FIG. 55.

EXAMPLE 10C

This concept can be extended to a higher number of cameras and phases according to the shown principle.

$N_{fluo} = n_{phases} \cdot n_{FluoCamsPerPhase} \cdot n_{CamChannels}$ $N_{refl} = n_{phases} \cdot n_{ReflCamsPerPhase} \cdot n_{CamChannels}$ There number of cameras is constant, so $n_{Cameras} = n_{FluoCamsPerPhase} + n_{ReflCamsPerPhase}$ This results in $N_{fluo} = n_{phases} \cdot (n_{Cameras} - n_{ReflCamsPerPhase}) \cdot n_{CamChannels}$ $N_{refl} = n_{phases} \cdot n_{ReflCamsPerPhase} \cdot n_{CamChannels}$ In the described scenario one camera is recording reflectance in each phase. This simplifies the formula to $N_{fluo} = n_{phases} \cdot (n_{Cameras} - 1) \cdot n_{CamChannels}$ $N_{refl} = n_{phases} \cdot 1 \cdot n_{CamChannels}$

|  | With $n_{CamChannels}$ not being fixed | | With $n_{CamChannels} = 3$ | |
|---|---|---|---|---|
| $n_{phases} = n_{Cameras}$ | $\frac{N_{fluo}}{n_{CamChannels}}$ | $\frac{N_{refl}}{n_{CamChannels}}$ | $N_{fluo}$ | $N_{refl}$ |
| 2 | 2 | 2 | 6 | 6 |
| 3 | 3 | 6 | 9 | 18 |
| 4 | 4 | 12 | 12 | 36 |
| 5 | 5 | 20 | 15 | 60 |
| 6 | 6 | 30 | 18 | 90 |
| 7 | 7 | 42 | 21 | 126 |
| 8 | 8 | 56 | 24 | 168 |
| 9 | 9 | 72 | 27 | 216 |
| 10 | 10 | 90 | 30 | 270 |

This means, that with 10 phases and 10 RGB cameras, a total of 30 reflection channels and 270 fluorescence channels can be recorded per image. The light intensity per channel is lower compared to a two camera setup, but therefore the number of spectral channels is higher which can also improve the output. So in theory, 270 different fluorescent components can be separated.

Of course such a setup puts high requirements on the hardware. For example it is challenging to design the respective filters for such a setup. This requires 10 different filters for the excitation and emission. The filters should be dual-band filter, so that if light source 10 is exciting fluorochromes, the sensors 1-9 can still record fluorescence. Of course it would be ideal if each of the filters are three band filters or multiband filters with a higher number of transmission bands.

Instead of using many individual cameras it is also possible to place the different images on one single chip one next to the other. This requires bigger sensors and a more sophisticated optical setup but saves the trouble of using and controlling many different cameras.

EXAMPLE 11

Figure 56:
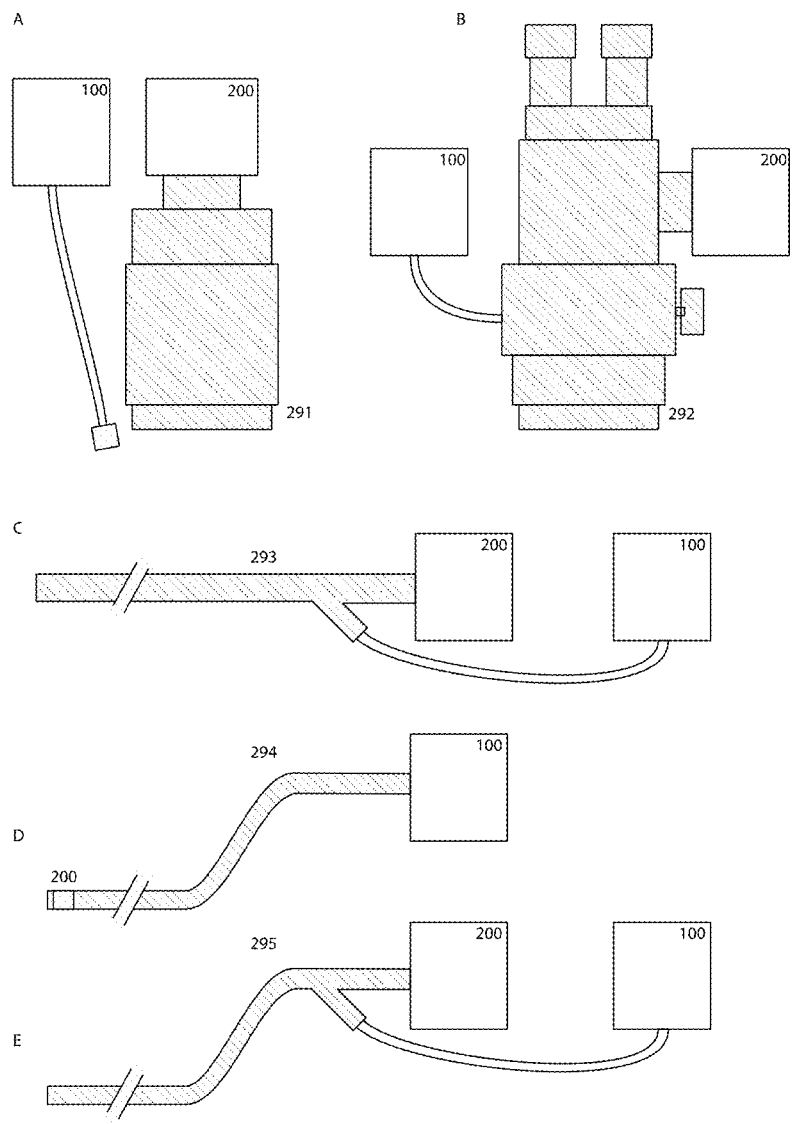
FIGS. 56A, 56B, 56C, 56D, and 56E show various apparatuses according to the invention.

The multispectral imaging method and system can be implemented by integrating into various imaging instruments, e.g. integrated in medical instruments. In a first embodiment as shown in FIG. 56A the multispectral imaging system is used with a zoom lens 291 as an objective lens by attaching the detector 200 with a camera adaptor, where the illumination system 100 delivers the light to the object with a light guide. In another integration as shown in FIG. 563 the detection system 200 is connected to the video port of a surgical microscope 292 and the illumination system 100 is connected with a light guide to the illumination port to illuminate the object through the objective lens of the microscope. In a further embodiment shown in FIG. 56C, the detection system 200 is connected to the eyepiece port of a rigid endoscope optionally with the use of an adaptor and the illumination system 100 is connected with a light guide to the illumination port. In a further embodiment of FIG.

56D the detection system 200 is miniaturized and integrated into the tip of a flexible endoscope, while the illumination system 100 is attached to the illumination port of the endoscope. In yet another embodiment as shown in FIG. 56E, the detection system 200 is connected to the camera port of the flexible fiberscope, which transfers the image from the tip to the distal point with the use of a flexible fiber bundle, and the illumination system 100 is connected to the illumination port.

EXAMPLE 12

Figure 57:
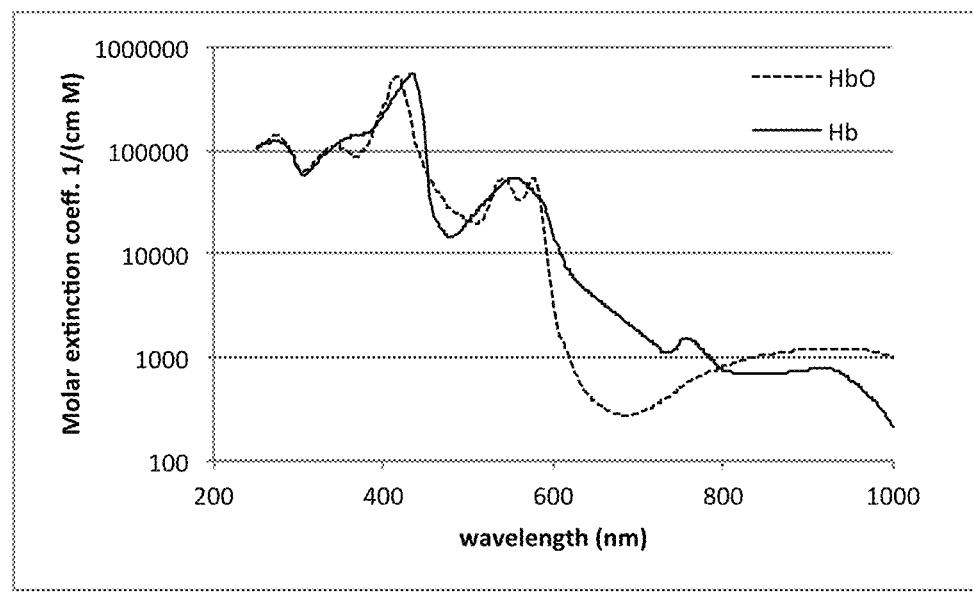
FIG. 57 shows the absorption spectra of Hb and HbO.

In the following several possible applications of the present inventive method are described.

a) Application Scenario: Imaging of blood oxygenation: In the following example oxygen saturation is imaged by assessing the relative concentration of oxygenated to deoxygenated hemoglobin (HbO and Hb) on tissue. Since HbO and Hb have distinct absorption spectra as shown in FIG. 57, the reflected light carries spectral profile information that can be recorded in the system. By spectrally unmixing the multiple reflectance components it is possible to generate a) an RGB image to be displayed in a visualization system and b) an additional map of the biodistribution of the HbO and Hb components. The oxygen saturation maps are calculated by the ratio between the HbO to the total hemoglobin saturation.

b) Application scenario: Detection of Cancer lesions, anatonimcal features, or functional conditions. Another envisioned application is to use the system to visualize the biodistribution of injectable fluorescent contrast agents for in-vivo clinical diagnostic imaging. These fluorescent contrast agents may be non-targeted, like Fluorescin or Indocyanin Green to highlight vascularization, blood perfusion etc., or targeted in a way that can highlight with fluorescence diseases, such as cancer, medical conditions, such as inflammation, or anatomical features, such as neures or lymph nodes, by binding to molecular sites associated to relative functional or pathological activity in tissue. An example is the imaging of glioblastoma tumors during brain surgery, using 5-ALA, a compound that induces the production of protoporphyrin in cancer cells. These applications may involve the integration of the invented method in medical imaging systems like surgical microscopes, endoscopes, laparoscopes, gastroscopes, broncoscopes, ophthalmoscopes, fundus cameras, etc.

c) Application Scenario: multi reporter imaging

Of particular interest is the application of the invented real time multispectral imaging technology in clinical applications utilizing dual reporter diagnostic approaches. The use of two or more fluorescent probes can provide diverse information on different biomarkers to access the pathological or functional condition of tissue. The combination of the biodistributions of different agents, that they come as image components after unmixing can enhance the visualization of a target to be imaged, i.e. a lesion, increase the detection sensitivity and specificity of a pathological feature.

d) Application Scenario: machine inspection

An additional envisioned application scenario of real time multispectral fluorescence imaging is on machine inspection. An engine or mechanical parts that are difficult to visually inspect, such as gears, because they are internally enclosed, may have damages like small cracks. These structural defects can be visualized after flushing the inside of the engine with a fluorescent solution and using an endoscope to inspect internally the location of cracks that retain the fluorescent fluid. Real time multispectral imaging can offer simultaneous color reflectance and fluorescence images.

e) Application Scenario: pH sensitive dyes

The chemical environment can influence the emission or the excitation of fluorescent dyes. One of these parameters changing the dye absorption and emission characteristics is the pH value.

Case of Emission Sensitive Dyes:

It is preferable to have the transmission bands of the respective filters optimized in a way to detect signal which is spectrally sensitive to changes of the pH value. It is also preferable to have detection channels which depend maximally on the pH value, whereas others are mostly insensitive to changes in pH value.

This can be realized for example by adjusting the emission filter bands such that the center of the respective measured fluorescence bands either match a spectral point where the dye emission spectrum varies maximal on a change of pH value or on a spectral point where the dye emission spectrum minimally depends on the pH value.

Case of Excitation Sensitive Dyes:

It is preferable to have the excitation bands of the respective filters and light sources optimized in a way to detect signal which is spectrally sensitive to changes of the pH value. It is also preferable to have excitation bands so that some of the detected channel(s) depend maximally on the pH value, whereas other channel(s) are mostly insensitive to changes of the pH value.

The excitation filter bands should be adjusted such that the center of the respective bands either matches a spectral point where the dye excitation spectrum varies maximal on a change of pH value or on a spectral point where the dye excitation spectrum minimally depends on the pH value.

The recorded images are multi spectrally recorded, spectrally unmixed and processed in such a way that they visualize the spatial distribution of the pH values.

f) Application Scenario: Distinguishing tumor infiltration zone and solid tumor mass by differences in the PPIX emission spectrum For tumor diagnostics, 5-ALA is administered to the patient leading to an accumulation of protoporphyrin IX (PPIX) in tumor tissue. The substance PPIX is both, a fluorescent dye and also an agent for photodynamic therapy.

The fluorescence emission spectrum of the PPIX varies depending on the location inside the tumor. More precisely the infiltration zone exhibits a different fluorescence emission spectrum compared to the solid tumor mass. This spectral difference can be used in order to differentiate between the tumor mass and the infiltration zone.

Two different peaked PPIX spectra with maxima at 620 nm and 635 nm can be recorded and unmixed with the inventive system.

In an imaging scenario of the second invention, the PPIX is preferably excited in both phases at approximately 405 nm. But in phase one, the emission is preferably recorded in a spectral band between 590 nm to 627 nm. In phase two, the fluorescence is preferably recorded in the spectral region between 628 nm to 650 nm.

Additionally, other fluorophores and also autofluorescence can be recorded.

g) Application Scenario: Autofluorescence

An interesting application is the spectral detection of the intrinsic tissue autofluorescence that is the fluorescence usually emitted without administering fluorescent contrast agents e.g. fluorophores. The tissue intrinsic autofluorescence is attributed to various molecules that exist or are produced in the tissues, such as NADPH, flavins, collagen, elastin, and others. The existence, production, accumulation, or other concentration properties is linked to various tissue features, such as anatomical, functional, and pathological features. The multispectral imaging of tissue autofluorescence and the spectral unmixing of the associated compounds according to the invention can reveal features or characteristics of tissue that aid the assessment or the diagnosis of a medical condition. Multispectral imaging and unmixing of the autofluorescence can take place together with systemically administered fluorescent molecules.

h) Application Scenario: Retina imaging

The retina can be imaged through the eye. Currently this imaging modality is used in clinical practice mainly for diagnostic purposes of the retina itself.

The eye provides a clear window to the blood vessels of the body looking directly in the retinal vessels. With multispectral imaging of the retina and spectral unmixing according to the invention it is possible to identify fluorescent molecules that are either existing in the retina or circulate in its blood vessels. These fluorescent molecules may have been systemically administered, to freely circulate or to target cells (possibly metastatic cancer cells), microorganisms, viruses, or molecules. Multispectral imaging and unmixing can identify these substances, which can provide information about the blood circulation in general, or the circulation of the targets, that can help to assess the functional, or pathological condition of the "patient". Therefore it is possible to use retina imaging to obtain information about the retina itself and also to obtain information about compounds circulating in the blood.

i) Application Scenario: Robotic surgery

An interesting application of the multispectral imaging and system is to combine it with a surgical robotic system. At a first place, it can provide the surgeon that operates with visual multispectral information either in the reflectance color domain, or in the (auto-)fluorescence domain, about tissue anatomy, function or disease. At a second level can provide input that increases the safety of the robot operation, for example prohibiting the doctor from accidentally damaging (i.e. cutting) tissue (for example, nerves). At a third level it can directly provide input and or feedback to an automated robotic surgery procedure that has reduced or minimum human controlling.

EXAMPLE 13

So far the described scenarios have the same number of phases (light sources) and sensors. Depending on the requirements, the principle of a system which uses combined temporal and spectral multiplexing also cover embodiments which have a different number of phases than cameras. Subsequently two different embodiments are described as examples. The first of those two scenarios has more cameras than phases (lights), while the second of those scenarios has more phases (lights) than cameras.

Spectral and Temporal Multiplexing with Two Phases (Lights) and Three Sensors

The embodiment which is described here with reference to FIG. 58 is derived from the basic embodiment shown in FIG. 3. It has one additional camera in the multispectral detector 200. This detector can record light also in both phases (from both lights). The additional sensor serves for example to record light in a spectral region, in which the other sensors are not sensitive, for example in the UV or more likely in the infrared region.

In our example, the spectral sensitivity of this additional monochrome sensor is high in the near infrared (NIR) region above 800 nm. So this sensor supports the other sensors by recording the light for example of a fluorescent dye emitting in the NIR such as ICG. Such dyes are desirable for clinical applications because they show less absorption in tissue by hemoglobin than dyes emitting in the blue or green region. Additionally this sensor can also record a reflection image in one of the two phases.

The system operates in two phases and thus has two lights. The lights need to match the spectral demands in the NIR region to provide excitation light for the fluorescent dye and also the provide illumination for reflection light to be recorded in the NIR region.

Excitation Scanning: Three Phases—Two Cameras

This part describes an embodiment which has more phases (lights) than cameras. The embodiment is derived from the basic embodiment, shown in FIG. 3. It has an additional phase and thus an additional third light. Thus one period of the imaging system is divided into three different acquisition phases.

This embodiment has additional capabilities to distinguish between dyes which have very similar emission spectra but very different excitation spectra.

If a strong absorber like hemoglobin in the blood is present sample, the recorded spectra of the emission of different dyes are governed by the changes in the absorption of the hemoglobin. So it is not possible anymore to distinguish between the emission spectra of two different dyes.

This is for example the case for dyes like protoporphyrin IX (PPIX) and Cy5, which both emit between 600 nm and 650 nm. In this region the absorptivity of hemoglobin changes by orders of magnitude and therefore it is not possible anymore to distinguish between the two different emissions.

In such a case excitation scanning can help to distinguish between the dyes. The emission of the two dyes in the same spectral region is recorded in two phases. But the excitation in these two phases needs to be different in order to be able to distinguish between the different dyes.

The invention claimed is:

1. A method for acquisition of fluorescence images and reflection images of an object, the method comprising the steps of:
    alternatingly illuminating the object with at least a first light and a second light, wherein the first light and the second light are spectrally shaped such that the first light has at least two spectral regions of high light intensity separated by spectral region(s) of low light intensity and the second light has at least one spectral region of high light intensity, wherein the spectral regions of the first light and the second light with the high light intensity at least partially do not overlap, wherein the first light and the second light have regions of low light intensity that are of longer wavelength to neighboring regions of high light intensity, wherein a ratio of the light intensity between at least one region of the high light intensity and at least one region of low light intensity for each of the first light and second light is $\geq 1 \times 10^2$, and
    recording at least a first image of the object and a second image of the object while illuminating the object with the first light, and recording at least the first image of the object and the second image of the object while illuminating the object with the second light,
    wherein the light to be recorded as the first image is modified such that at least the one spectral region of the high light intensity of the second light is attenuated, and wherein the light to be recorded as the second image is modified such that at least the two spectral regions of the high light intensity of the first light are attenuated, wherein both of the first and second images are recorded by at least one or two sensor arrays, wherein the first image and the second image are one of:

a) recorded with different sensor arrays, which are located each in a partial light path, and b) recorded with two distinct regions of a single sensor array, wherein the two distinct regions of the sensor array are located each in a partial light path and at least partially do not overlap, wherein in at least one of a) and b) the partial light paths are generated by splitting the light emanating from the object into two partial lights wherein each of the sensor arrays is a multichannel array, where each channel has a distinct spectral sensitivity, and wherein at least one of a) the attenuation ratio between the intensity of the unattenuated to the attenuated spectral regions of the light to be recorded is $\geq 1 \times 10^2$, and b) the amount of attenuation of the light to be recorded as the first image in at least one spectral region of the high light intensity of the second light is such that the intensity of the light recorded in the unattenuated spectral region is higher than the intensity of the light recorded in the sum of the attenuated spectral regions.

2. The method according to claim 1, wherein one or both sensor arrays are color sensor arrays.

3. The method according to claim 1, wherein at least one of the first image, which is recorded when the object is illuminated with the first light, and the second image, which is recorded when the object is illuminated with the second light, are composed to generate a first composite image, and the first image, which is recorded when the object is illuminated with the second light, and the second image, which is recorded when the object is illuminated with the first light, are composed to generate a second composite image.

4. The method according to claim 3, wherein the first image and second image are images recorded subsequent to each other.

5. The method according to claim 1, wherein the data, which are provided in the channel image space of the recorded images are transformed into values of a component image space, where the components are the spatial distributions of fluorochromes, absorbers, derived values, or noise.

6. The method according to claim 1, wherein the ratio of the light intensity between at least one region of the high light intensity at shorter wavelength and at least one region of low light intensity of longer wavelength for at least one of the lights is $\geq 1 \times 10^3$.

7. The method according to claim 1, wherein at least one of the first light and the second light are generated by one of:

a) by broadband lights or white light, from two broadband light sources, wherein said broadband lights are filtered by multiple bandpass filters in order to generate the first light and the second light, wherein the at least two multiple bandpass filters have complementary spectral transmission characteristics, b) by multiple narrowband light sources, or light emitting diodes (LED), and c) by a combination of broadband light sources according to a) and multiple individual LEDs according to b).

8. The method according to claim 1, wherein the light recorded as the first image and the light recorded as the second image are filtered using multiple bandpass filters, wherein the multiple bandpass filter used to filter the light to be recorded as the first image has spectral transmission characteristics, which are complementary to the spectral transmission characteristics of the filter used to filter the light to be recorded as the second image.

9. The method according to claim 8, wherein the multiple bandpass filters which are used to filter the light to be recorded as the first image and used to filter the light to be recorded as the second image have transmission characteristics corresponding to the spectral shape of the first light and the second light, respectively.

10. The method according to claim 1, wherein the number of images recorded is the same or less than the number of different lights alternatively illuminating the object.

11. The method according to claim 1, wherein one of:

alternatingly illuminating the object with at least the first light, having a first illumination period, and the second light, having a second illumination period, and illuminating the object with pulses of a further light, wherein the pulse duration of the further light is short compared to the first illumination period and short compared to the second illumination period, and holding the recording of the first image and the second image during said illumination with further light, and alternatingly illuminating the object with at least the first light, having a first illumination period, the second light, having a second illumination period, and a third light having a third illumination period.

12. The method according to claim 1, wherein the amount of attenuation of the light to be recorded as the second image in at least one spectral region of high intensity of the first light is such that the intensity of the light recorded in the unattenuated spectral region is higher than the intensity of the light recorded in the sum of the attenuated spectral regions.

13. An imaging apparatus for acquisition of fluorescence images and reflection images of an object, the imaging apparatus comprising:

at least a first light source and a second light source configured to alternatingly illuminate the object with at least a first light from the first light source and a second light from the second light source, wherein the first light is spectrally shaped such that the first light has at least two spectral regions of high light intensity separated by spectral region(s) of low light intensity and the second light is spectrally shaped such that the second light has at least one spectral region, wherein the spectral regions of the first light and the second light with the high light intensity at least partially do not overlap and wherein the first light and the second light have regions of low light intensity that are of longer wavelength to a neighboring region of high light intensity, wherein the ratio of the light intensity between at least one region of the high light intensity and at least one region of low light intensity for each of the first light and the second light is $\geq 1 \times 10^2$, and at least one of a first sensor and a second sensor, the at least one or both sensors being configured to record a first image of the object and a second image of the object while illuminating the object with the first light, and to record the first image and the second image of the object while illuminating the object with the second light, wherein each of the first sensor and the second sensor is a multichannel array, where each channel has a distinct spectral sensitivity, wherein the first image and the second image are one of:
a) recorded with different sensor arrays, which are located each in a partial light path, and
b) recorded with two distinct regions of a single sensor array, wherein the two distinct regions of the sensor array are located each in a partial light path and at least partially do not overlap, wherein in at least one of a) and b) the partial light paths are generated by splitting the light emanating from the object into two partial lights, a first filter configured to modify the light recorded as the first image such that at least the one spectral region of the high light intensity of the second light is attenuated, a second filter configured to modify the light recorded as the second image such that at least two spectral regions of the high light intensity of the first light are attenuated, and at least one of:
a) the attenuation ratio between the intensity of the unattenuated to the attenuated spectral regions of the light to be recorded is $\geq 1 \times 10^2$, and
b) the amount of attenuation of the light to be recorded as the first image in at least one spectral region of the high light intensity of the second light is such that the intensity of the light recorded in the unattenuated spectral region is higher than the intensity of the light recorded in the sum of the attenuated spectral regions.

14. The imaging apparatus according to claim 13, wherein at least one or both of the sensor arrays are color sensor arrays.

15. The imaging apparatus according to claim 13, wherein at least one of:
a) the first sensor array is configured to record the first image when the object is illuminated with the first light and the second sensor array is configured to record the second image when the object is illuminated with the second light and a composing unit configured to compose said first image and said second image to generate a first composed image, and
b) the first sensor array is configured to record the first image when the object is illuminated with the second light and the second sensor array is configured to record the second image when the object is illuminated with the first light and a second composing unit configured to compose said first image and said second image to generate a second composed image.

16. The imaging apparatus according to claim 15, wherein the first image and the second image are images recorded subsequent to each other.

17. The imaging apparatus according to claim 13, wherein the ratio of the light intensity between at least one region of high intensity at shorter wavelength and at least one region of low light intensity of longer wavelength for at least one of the lights is $\geq 1 \times 10^3$.

18. An endoscope or a surgical microscope comprising an imaging apparatus according to claim 13.

19. A use of a method, apparatus, endoscope or surgical microscope according to claim 13 for recording reflection images or for at least one of (a) internal inspection in automotive applications, (b) in medical diagnostics, (c) in medical treatment, (d) in chemical analysis and (e) in physical analysis.

20. The imaging apparatus according to claim 13, wherein the amount of attenuation of the light to be recorded as the second image in at least one spectral region of high intensity of the first light is such that the intensity of the light recorded in the unattenuated spectral region is higher than the intensity of the light recorded in the sum of the attenuated spectral regions.

* * * * *